United States Patent
Iannotti et al.

(10) Patent No.: US 9,741,263 B2
(45) Date of Patent: Aug. 22, 2017

(54) SYSTEM OF PREOPERATIVE PLANNING AND PROVISION OF PATIENT-SPECIFIC SURGICAL AIDS

(71) Applicant: THE CLEVELAND CLINIC FOUNDATION, Cleveland, OH (US)

(72) Inventors: Joseph P. Iannotti, Strongsville, OH (US); Wael K. Barsoum, Bay Village, OH (US); Jason A. Bryan, Avon Lake, OH (US); Peter D. O'Neill, Shaker Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 325 days.

(21) Appl. No.: 13/864,558

(22) Filed: Apr. 17, 2013

(65) Prior Publication Data
US 2013/0230838 A1 Sep. 5, 2013

Related U.S. Application Data

(63) Continuation-in-part of application No. 13/282,550, filed on Oct. 27, 2011.
(Continued)

(51) Int. Cl.
*A61B 5/00* (2006.01)
*G09B 23/28* (2006.01)
(Continued)

(52) U.S. Cl.
CPC .......... *G09B 23/28* (2013.01); *A61B 17/1739* (2013.01); *A61B 34/10* (2016.02);
(Continued)

(58) Field of Classification Search
CPC ... A61B 19/50; A61B 17/15; A61B 2019/505; A61B 17/157; A61B 19/5244;
(Continued)

(56) References Cited

U.S. PATENT DOCUMENTS 4,714,470 A * 12/1987 Webb et al. ............... 623/23.44
4,976,737 A    12/1990 Leake
(Continued)

FOREIGN PATENT DOCUMENTS

EP    0558789    9/1993

OTHER PUBLICATIONS

Valstar et al. ("Towards computer-assisted surgery in shoulder joint replacement", ISPRS Journal of Photogrammetry & Remote Sensing 56 (2002) pp. 326-337).*
(Continued)

*Primary Examiner* — Omar Fernandez Rivas
*Assistant Examiner* — Iftekhar Khan
(74) *Attorney, Agent, or Firm* — Tarolli, Sundheim, Covell & Tummino LLP

(57) ABSTRACT

A method for assisting a user with surgical implementation of a preoperative plan includes generating a physical native tissue model of a native patient tissue. The physical native tissue model includes at least one primary patient tissue area including a surface of interest, at least one secondary patient tissue area including no surfaces of interest, and a base surface for engaging a supporting structure. The physical native tissue model, as generated, includes at least one information feature providing clinically useful information to the user. The information feature is substantially separated from the surface of interest. An apparatus for assisting a user with surgical implementation of a preoperative plan is also provided.

34 Claims, 34 Drawing Sheets

Related U.S. Application Data

(60) Provisional application No. 61/408,392, filed on Oct. 29, 2010.

(51) Int. Cl.
| | | |
|---|---|---|
| *A61F 2/40* | (2006.01) | |
| *A61B 17/17* | (2006.01) | |
| *G09B 23/30* | (2006.01) | |
| *G09B 23/32* | (2006.01) | |
| *G09B 23/34* | (2006.01) | |
| *A61B 34/10* | (2016.01) | |
| *A61B 17/56* | (2006.01) | |
| *A61F 2/46* | (2006.01) | |
| *A61B 34/00* | (2016.01) | |

(52) U.S. Cl.
CPC .......... *A61F 2/4081* (2013.01); *G09B 23/30* (2013.01); *G09B 23/32* (2013.01); *G09B 23/34* (2013.01); *A61B 17/1778* (2016.11); *A61B 34/25* (2016.02); *A61B 2017/568* (2013.01); *A61B 2034/105* (2016.02); *A61B 2034/108* (2016.02); *A61F 2002/4633* (2013.01)

(58) Field of Classification Search
CPC .......... A61B 2019/508; A61B 17/1666; A61B 17/1721; A61B 17/683; A61B 19/5225
USPC ................ 434/262; 606/87, 88, 91; 623/23; 705/2, 3
See application file for complete search history.

(56) References Cited

U.S. PATENT DOCUMENTS

| | | | |
|---|---|---|---|
| 5,098,383 | A | 3/1992 | Hemmy et al. |
| 5,682,886 | A | 11/1997 | Delp et al. |
| 5,768,134 | A | 6/1998 | Swaelens et al. |
| 5,871,018 | A | 2/1999 | Delp et al. |
| 6,205,411 | B1 | 3/2001 | DiGioia, III et al. |
| 6,327,491 | B1 | 12/2001 | Franklin et al. |
| 6,711,432 | B1 | 3/2004 | Krause et al. |
| 6,772,026 | B2 | 8/2004 | Bradbury et al. |
| 7,194,120 | B2 | 3/2007 | Wicker et al. |
| 7,542,791 | B2 * | 6/2009 | Mire et al. ............... 600/407 |
| 7,702,380 | B1 * | 4/2010 | Dean ............... 600/426 |
| 2004/0068187 | A1 | 4/2004 | Krause et al. |
| 2005/0148843 | A1 | 7/2005 | Roose |
| 2007/0173815 | A1 | 7/2007 | Murase |
| 2007/0198022 | A1 | 8/2007 | Lang et al. |
| 2007/0250177 | A1 * | 10/2007 | Bilbo ............... 623/23.72 |
| 2007/0288030 | A1 | 12/2007 | Metzger et al. |
| 2008/0114370 | A1 | 5/2008 | Schoenefeld |
| 2008/0138781 | A1 * | 6/2008 | Pellegrin et al. ............... 434/274 |
| 2008/0269906 | A1 | 10/2008 | Iannotti et al. |
| 2008/0287954 | A1 | 11/2008 | Kunz et al. |
| 2009/0018546 | A1 | 1/2009 | Daley |
| 2009/0131941 | A1 | 5/2009 | Park et al. |
| 2009/0163922 | A1 | 6/2009 | Meridew et al. |
| 2009/0254367 | A1 * | 10/2009 | Belcher et al. ............... 705/2 |
| 2009/0318929 | A1 * | 12/2009 | Tornier et al. ............... 606/99 |
| 2010/0152782 | A1 | 6/2010 | Stone et al. |
| 2010/0191244 | A1 * | 7/2010 | White et al. ............... 606/88 |
| 2011/0040303 | A1 | 2/2011 | Iannotti |
| 2011/0190775 | A1 | 8/2011 | Ure |
| 2011/0295378 | A1 * | 12/2011 | Bojarski et al. ............... 623/20.35 |
| 2012/0022843 | A1 * | 1/2012 | Ionasec et al. ............... 703/9 |

OTHER PUBLICATIONS

Strauss et al("The glenoid in shoulder arthroplasty", Journal Shoulder Elbow Surg (2009) 18, 819-833).*
Matthews et al.("Patient-Specific Three-Dimensional Composite Bone Models for Teaching and Operation Planning ", for Imaging Informatics in Medicine, 2007, pp. 1-10).*
Krekel, et al., Interactive Simulation and Comparative Visualisation of the . . . , Data Visualisation Group, Deltf Univ. of Technology, pp. 1-13.
Krekel, et al., Combined Surface and Volume Processing for Fused Joint Segmentation, Springer Int'l. Journal of Computer Assisted Radiology and Surgery, pp. 1-24.
Krekel, et al., Visual Analysis of Multi-Joint Kinematic Data, Eurographics/IEEE-VGTC Symposium on Visualization 2010, vol. 29 (2010), No. 3, pp. 1-10.
Krekel, et al., Evaluation of Bone Impingement Prediction in Preoperative Planning for Shoulder Arthroplasty, Proc. IMechE vol. 223, Part H: J. Engin. in Med., 2009, pp. 1-10.
Botha, et al., Pre-Operative Planning and Intra-Operative Guidance for Shoulder Replacement Surgery, Dagstuhl Publ., pp. 179-195.
Murphy, et al., The Planning of Orthopaedic Reconstructive Surgery Using Computer-Aided Simulation and Design, Comp. Med. Imag. and Graphics, 12:33-45 (1988).
U.S. Iannotti et al., U.S. Appl. No. 61/408,324, filed, Oct. 29, 2010, entitled System and Method for Assisting With Attachment of a Stock Implant to a Patient Tissue.
U.S. Iannotti et al., U.S. Appl. No. 61/408,359, filed, Oct. 29, 2010, entitled System and Method for Association of a Guiding Aid With a Patient Tissue.
U.S. Iannotti et al., U.S. Appl. No. 61/408,376, filed, Oct. 29, 2010, entitled System and Method for Assisting With Arrangement of a Stock Implant With Respect to a Patient Tissue.

* cited by examiner

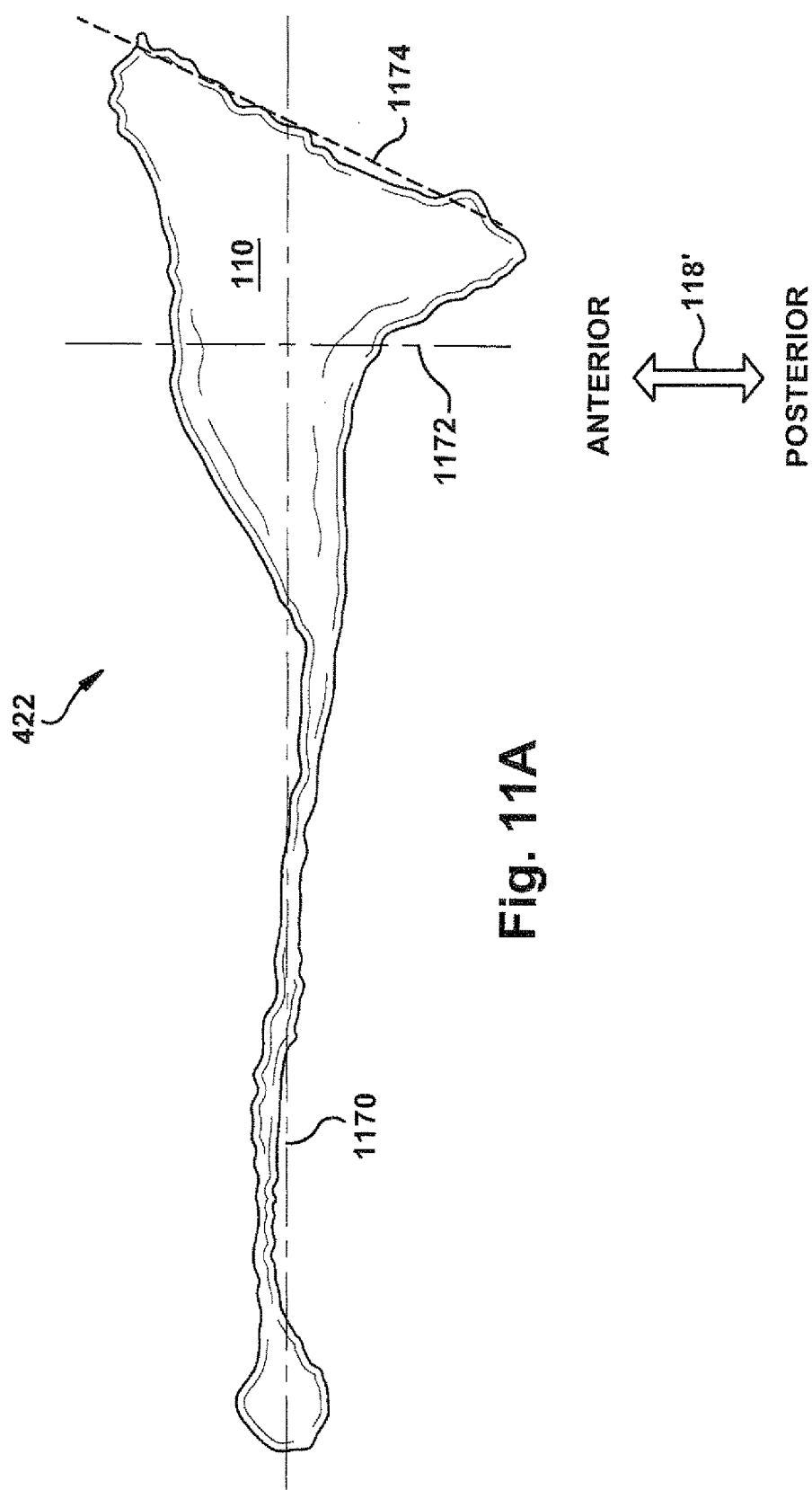

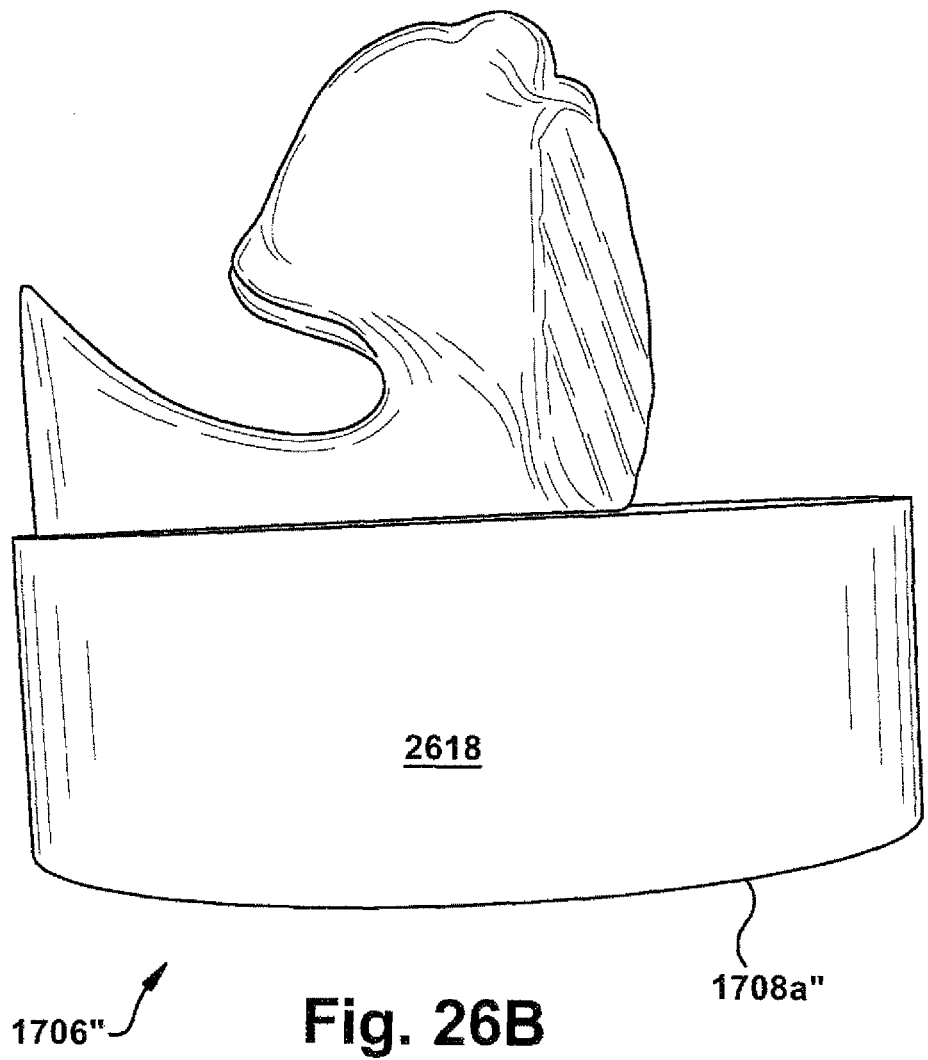

SYSTEM OF PREOPERATIVE PLANNING AND PROVISION OF PATIENT-SPECIFIC SURGICAL AIDS

RELATED APPLICATION

This application is a continuation-in-part of U.S. patent application Ser. No. 13/282,550, filed 27 Oct. 2011 and claiming priority to U.S. Provisional Application No. 61/408,392, filed 29 Oct. 2010, the subject matter of both of which is incorporated herein by reference.

TECHNICAL FIELD

The present invention relates to a preoperative planning system and, more particularly, to a system of preoperative planning and provision of patient-specific surgical aids.

BACKGROUND OF THE INVENTION

The scapula, commonly known as the "shoulder blade", is a flat, triangular bone that lies over the back of the upper ribs. A right scapula 100 is depicted in posterior, anterior, and right side views in FIGS. 1A, 1B, and 1C, respectively. The posterior surface of the scapula 100 can be readily felt through a patient's skin. The scapula 100 serves as an attachment point for some of the muscles and tendons of the arm, neck, chest, and back, and aids in the movements of the arm and shoulder. The scapula 100 is also well padded with muscle, so that it may be difficult to palpate boney landmarks. The rear surface of each scapula 100 is divided into unequal portions by a spine 102. This spine 102 leads to a head 104, which ends in the acromion process 106. A coracoid process 108 forms a prominence of the shoulder that curves forward and down below the clavicle (collarbone, not shown). The acromion process 106 joins the clavicle and provides attachments for muscles of the arm and chest muscles. The acromion process 106 is a bony prominence at the top of the scapula 100. On the head 104 of the scapula 100, between the acromion and coracoid processes 106 and 108, is a depression or cavity called the glenoid vault 110, shown partially in dashed line in the Figures. The glenoid vault 110 joins with the head of the upper arm bone (humerus, not shown) in a ball-and-socket manner to enable articulation of the shoulder joint thereby formed. Similarly, though not shown, an acetabulum of the hip joins with a head of an upper leg bone (femur) to form an analogous ball-and-socket manner for hip joint articulation.

For treatment of various problems with the shoulder, hip, or other body joint or bone (such as degenerative arthritis and/or traumatic injury), one method of providing relief to a patient is to replace the articulating surfaces with an artificial or prosthetic joint. In the case of a shoulder, the humerus and glenoid vault 110 articulating surfaces are replaced or resurfaced. In the case of a hip, the femur and acetabulum articulating surfaces can be replaced or resurfaced. Both of these examples are of ball-and-socket type joints. Hinge-type joints, such as the knee or elbow, and static/fixed skeletal components, such as the long bones of the arm or leg, as well as interfaces such as those between spinal vertebrae and intervertebral discs, could also be subject to replacement and/or repair by the implantation of artificial or prosthetic components or other fixation devices related to the treatment of fractures, the sequelae of trauma, congenital pathology, or other issues causing a lack of ideal function. For clarity of description, the subject application will be hereafter described as the rehabilitation and/or replacement of a patient's shoulder joint.

In such surgical procedures, pain relief, increased motion, and/or anatomic reconstruction of the joint are goals of the orthopedic surgeon. With multiple variations in human anatomy, prosthetic systems must be carefully designed, chosen, and implanted to accurately replicate the joints that they replace or the bone structures that they aim to change (in any manner).

A shoulder replacement procedure may involve a partial shoulder replacement (not shown) or the total shoulder replacement shown in FIG. 2. In a total shoulder replacement procedure, a humeral component 212 having a head portion is utilized to replace the natural head portion of the upper arm bone, or humerus 214. The humeral component 212 typically has an elongated stem which is utilized to secure the humeral component to the patient's humerus 214, as depicted. In such a total shoulder replacement procedure, the natural bearing surface of the glenoid vault 110 is resurfaced, lined, or otherwise supplemented with a cup-shaped glenoid component 216 that provides a bearing surface for the head portion of the humeral component 212. The depicted total shoulder replacement of FIG. 2 is an "anatomical" shoulder replacement. A "reverse" shoulder replacement is also known in the art.

Standard prosthetic glenoid components 216 are available in a number of different sizes and configurations. However, most are designed for use in an scapula having minimal bone loss or deformity. When the scapula has bone loss and/or significant pathology due to disease or trauma, the standard glenoid component 216 may be difficult to implant and/or may not enable desired shoulder function, if it cannot be implanted in a preferred manner. The surgeon may thus need to substantially modify the patient's glenoid vault 110 during surgery in an attempt to make the standard glenoid component 216 fit into the glenoid vault. Presurgical planning tools are available to help the surgeon anticipate the changes which will be needed to reform the patient's pathological anatomy. However, the surgeon cannot always readily determine whether even a remodeled glenoid vault 110 will fit as desired with a standard prosthesis because the surgeon does not know how a "normal" glenoid vault 110 (for which the standard prosthesis is designed) should be shaped for that patient.

It is known to use computer aided design ("CAD") software to design custom prostheses based upon imported data obtained from a computerized tomography ("CT") scan of a patient's body. For example, mirror-imaged CT data of a patient's contralateral "normal" joint could be used, if the contralateral joint does not also display a pathological anatomy. However, using a unique prosthesis design for each patient can result in future biomechanical problems resulting from a non-proven design and takes away the familiarity that the surgeon will likely have with standardized prosthesis designs. Thus, prosthesis designs that are entirely customized are considered sub-optimal solutions and may also be extremely expensive to design and produce.

Further, detailed preoperative planning, using two- or three-dimensional images of the shoulder joint, often assists the surgeon in compensating for the patient's anatomical limitations. During the surgery, for example, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. For example, in a shoulder surgery, the scapula 100 is mobile along the posterior and lateral chest walls and it therefore may be difficult to define the fixed relationship of the glenoid vault 110 to the body of the scapula 100 (i.e., using the plane of the scapula as a reference to the glenoid vault) and/or the body of the scapula to an external coordinate system in the operating room. These factors, particularly in a minimally invasive surgical procedure, may make it difficult for the surgeon to orient the glenoid vault during surgery. Again, a guide pin may be temporarily or permanently placed into the exposed bone surface to help orient the surgeon and thereby enhance the accuracy and efficiency of the surgical procedure.

One goal of shoulder surgery may be to modify the pathologic bone to correct pathologic position to be within the normal range or the normal position of the patient's native anatomy before the bone loss occurred. During surgery, and particularly minimally invasive procedures, the plane of the scapula may be difficult or impossible to determine by direct visual inspection, resulting in the need for assistive devices or methods to define both the pathologic version present at the time of surgery and the intended correction angle.

It is generally believed that there is a preferred orientation for the glenoid component 216 to provide a full range of motion and to minimize the risk of dislocation. Some example orientations of the glenoid component 216 relative to the glenoid face are about 5° of anteversion to about 15° of retroversion; average version is about 1-2° of retroversion. This broadly replicates the natural angle of the glenoid. However, the specific angular orientation of the glenoid portion, as well as the offset and inclination of the glenoid, varies from patient to patient.

With a view to overcoming these and other disadvantages, some arrangements have been recently suggested in which a three-dimensional intraoperative surgical navigation system is used to render a model of the patient's bone structure. This model is displayed on a computer screen and the user is provided with intraoperative three-dimensional information as to the desired positioning of the instruments and the glenoid component 216 of the prosthetic implant. However, surgical navigation arrangements of this type are not wholly satisfactory since they generally use only a low number of measured landmark points to register the patient's anatomy and to specify the angle of the prosthetic implant component (e.g., a glenoid component 216), which may not provide the desired level of accuracy. Further, the information provided by such systems may be difficult to interpret and may even provide the user with a false sense of security. Moreover, these systems are generally expensive to install and operate and also have high user training costs.

Various proposals for trial prosthetic joint components have been made in an attempt to overcome the problems associated with accurately locating the glenoid component 216 of the prosthetic implant. While these trial systems may help with checking whether the selected position is correct, they are not well-suited to specify the correct position initially, and thus there still is user desire for a system which may assist a user in placement of prosthetic implant component in a prepared native tissue site.

Finally, due to factors such as the high cost of operating room time and the patient detriment sometimes posed by lengthy surgeries, the surgeon or other user may wish to simulate a surgical procedure during preoperative planning, in order to become familiar with the tasks that will be required and possibly reduce the time and/or actions needed to perform the surgery.

In summary, preoperative planning and/or simulation, regardless of the planning tasks undertaken or the nature of the changes to be made to the patient's native tissue, will generally reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, a method for assisting a user with surgical implementation of a preoperative plan is disclosed. A physical native tissue model of a native patient tissue is generated. The physical native tissue model includes at least one primary patient tissue area including a surface of interest, at least one secondary patient tissue area including no surfaces of interest, and a base surface for engaging a supporting structure. The physical native tissue model, as generated, includes at least one information feature providing clinically useful information to the user. The information feature is substantially separated from the surface of interest.

In an embodiment of the present invention, an apparatus for assisting a user with surgical implementation of a preoperative plan is disclosed. A physical native tissue model of a native patient tissue includes at least one primary patient tissue area including a surface of interest, and at least one secondary patient tissue area including no surfaces of interest. At least one information feature provides clinically useful information to the user. The information feature is included in the physical native tissue model as generated. The information feature is substantially separated from the surface of interest.

In an embodiment of the present invention, a method of preoperative planning for assisting a user with surgical implementation of a preoperative plan is disclosed. A physical native tissue model of a native patient tissue is generated. The physical native tissue model includes at least one surface of interest and a base surface, spaced apart from the surface of interest, for engaging a supporting structure. The physical native tissue model, as generated, includes at least one information feature providing clinically useful information to the user. The information feature includes at least one of: a landmark indicating at least one of a marking location and a marking trajectory to which reference is made during surgical modification of the native patient tissue, the landmark being spaced apart from the surgical modification location; a predetermined orientation of the base surface which is operative to position at least one surface of interest in a predetermined orientation in space when the base surface is engaged with the supporting structure; and a replica of at least a portion of a prosthetic implant in a preoperatively planned installed position.

In an embodiment of the present invention, a method of preoperative planning for assisting a user with surgical implementation of a preoperative plan is disclosed. A physical native tissue model of a native patient tissue is generated.

The physical native tissue model includes at least one surface of interest and a base surface, spaced apart from the surface of interest, for engaging a supporting structure. The physical native tissue model, as generated, includes at least one information feature providing clinically useful information to the user. The clinically useful information is information other than a desired location for material modification of the native patient tissue.

BRIEF DESCRIPTION OF THE DRAWINGS

For a better understanding of the invention, reference may be made to the accompanying drawings, in which:

FIGS. 11A-11B are schematic views depicting a use environment for the embodiment of FIG. 3;

FIGS. 26A-26D are perspective views of a physical native tissue model.

DESCRIPTION OF EMBODIMENTS

The patient tissue is shown and described herein at least as a scapula 100 and the prosthetic implant component is shown and described herein at least as a glenoid component 216, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention. For example, the prosthetic implant component could be an internal fixation device (e.g., a bone plate), a structure of a replacement/prosthetic joint, or any other suitable artificial device to replace or augment a missing or impaired part of the body.

Figures 1A, 1B:
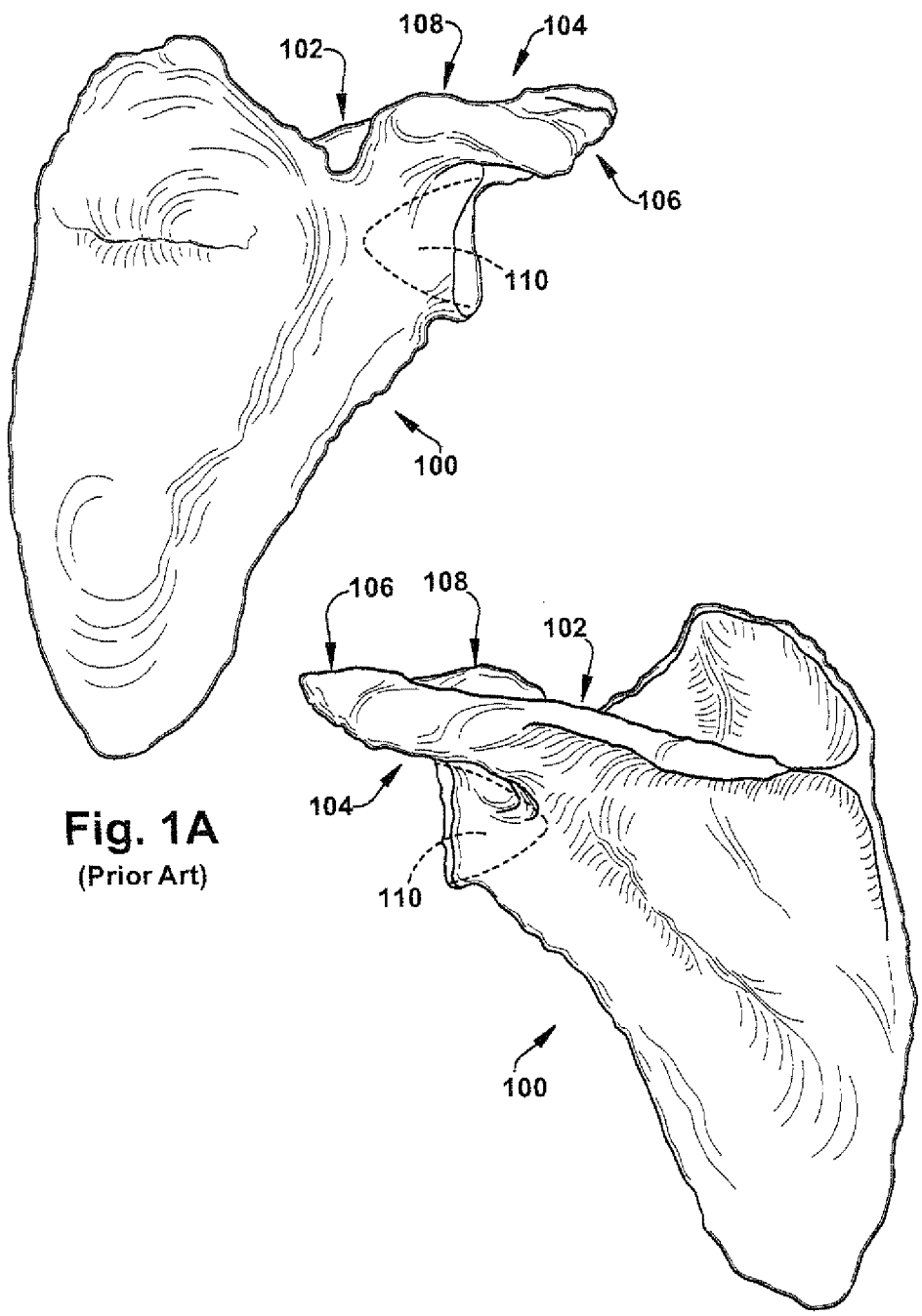
FIG. 1A is an anterior view of a right scapula.
FIG. 1B is a posterior view of the scapula of FIG. 1A.
Figure 1C:
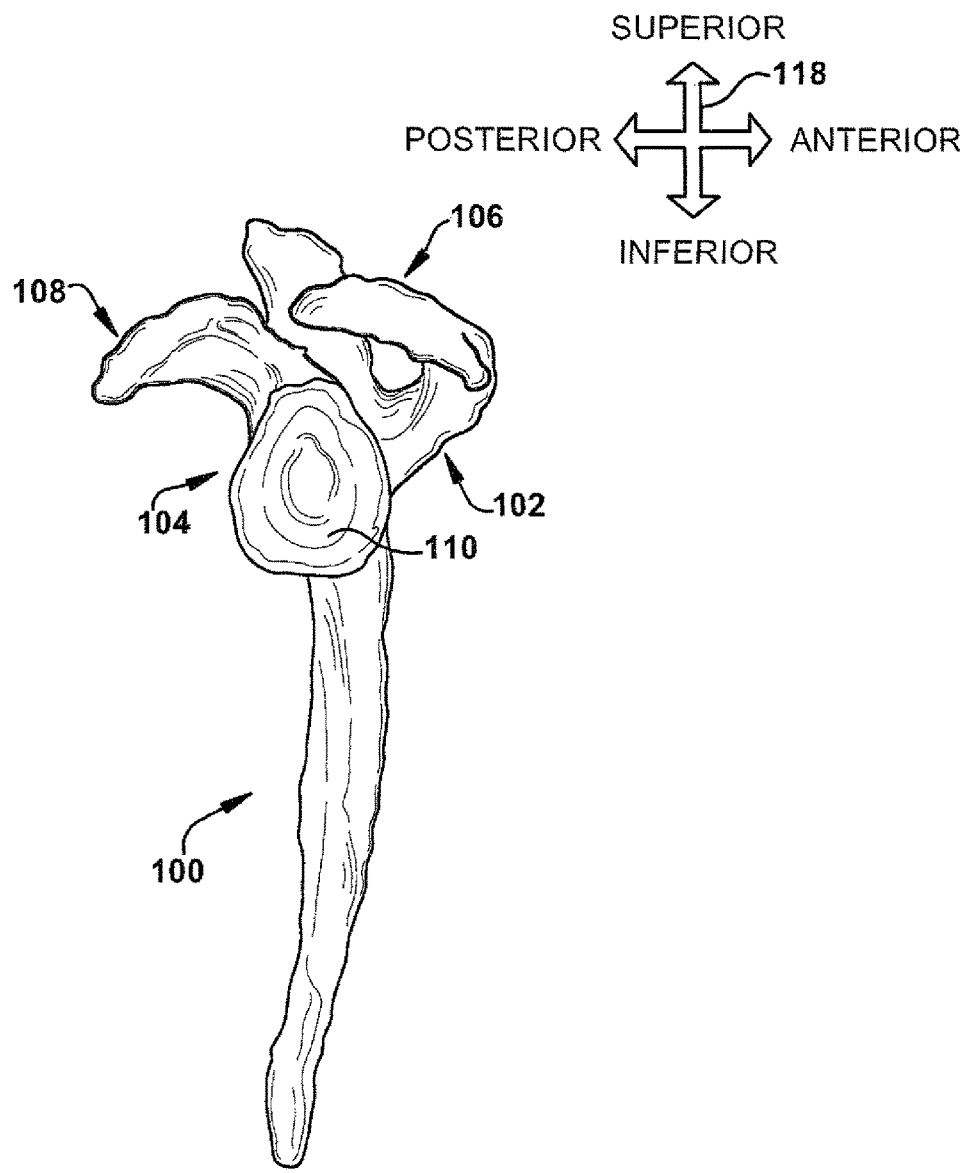
FIG. 1C is a side view of the scapula of FIG. 1A.
Figure 2:
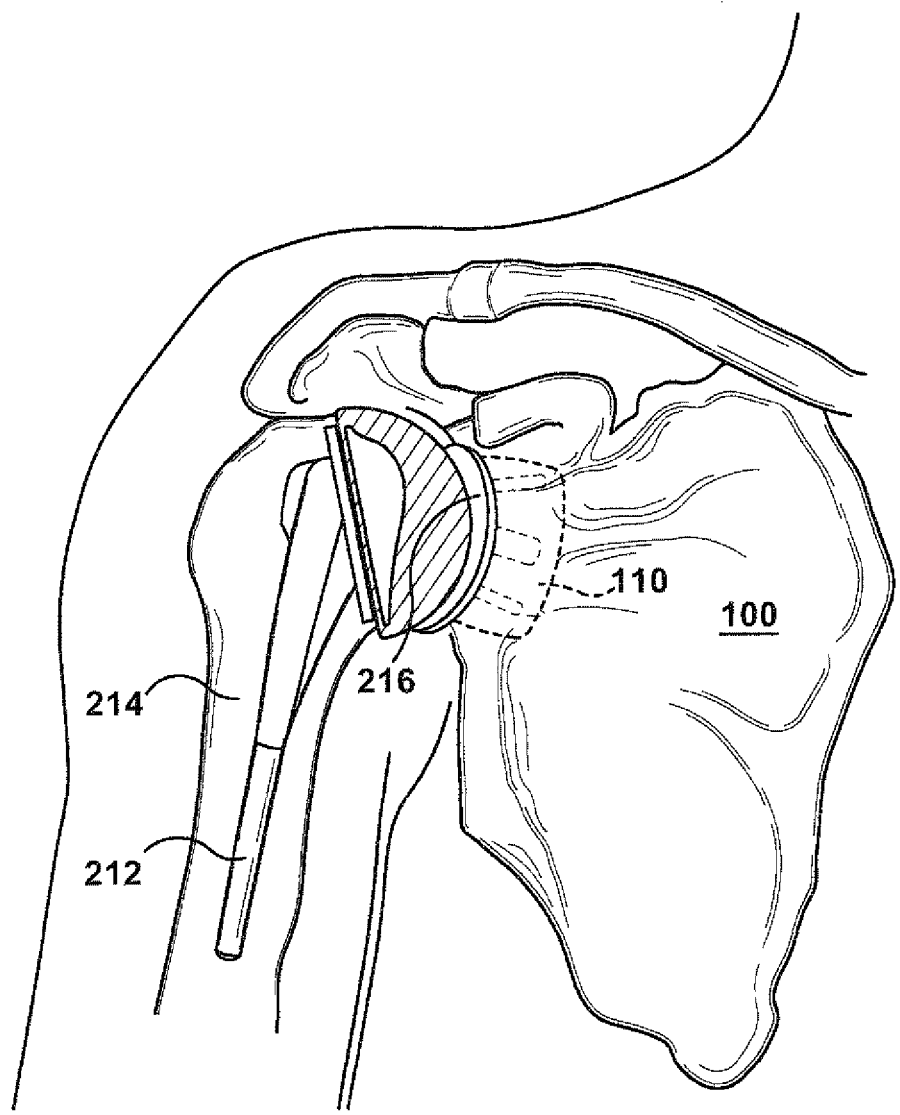
FIG. 2 is a partial sectional anterior view of a prosthetic shoulder joint in a patient.
Figure 10:
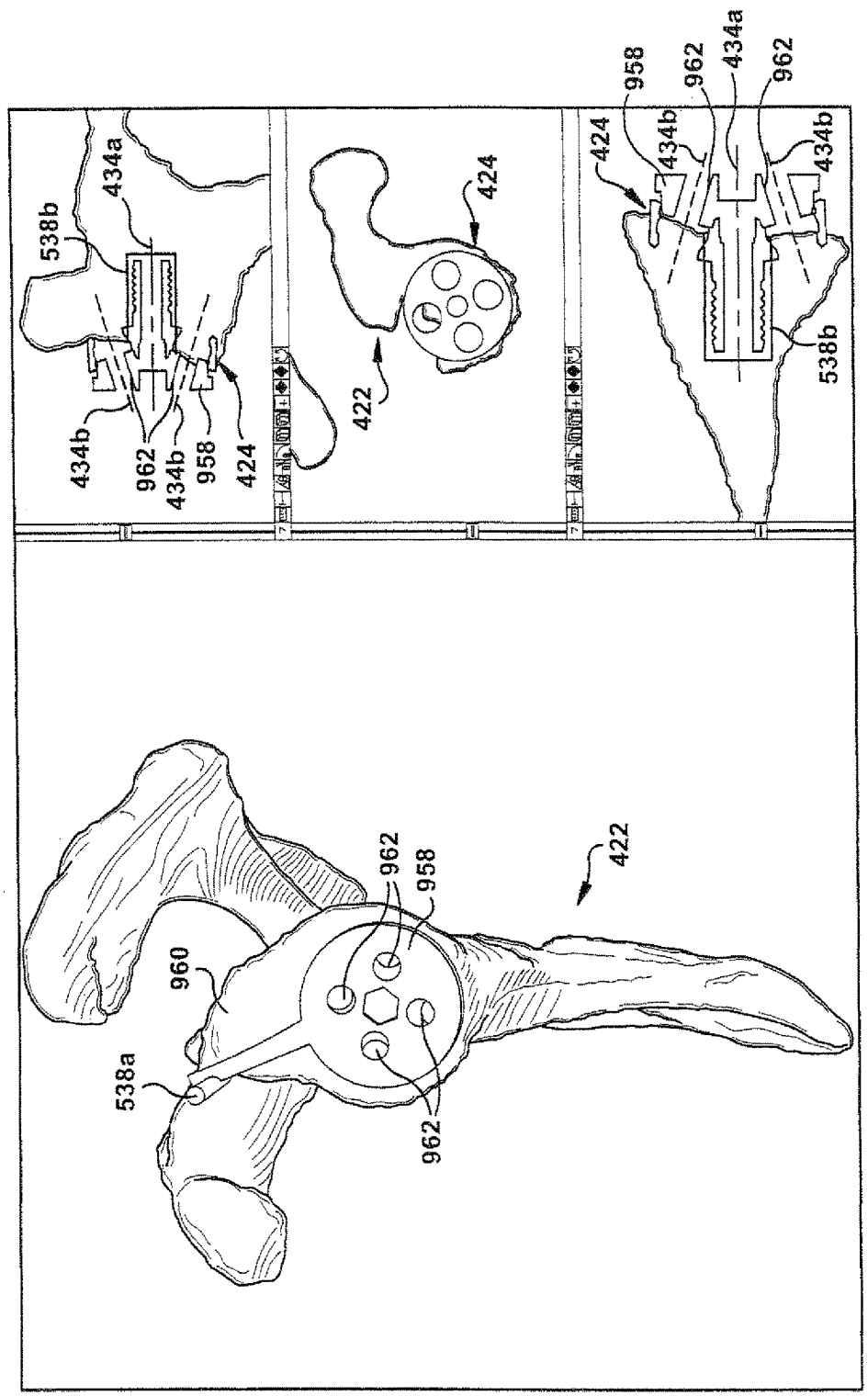

The term "lateral" is used herein to refer to a direction indicated by directional arrow 118 in FIG. 10; the lateral direction in FIG. 1C lies substantially within the plane of the drawing and includes all of the superior, inferior, anterior, and posterior directions. The term "longitudinal" is used herein to refer to a direction defined perpendicular to the plane created by directional arrow 118, with the longitudinal direction being substantially into and out of the plane of the drawing in FIG. 1C and representing the proximal (toward the medial line of the body) and distal (out from the body) directions, respectively.

Figure 3:
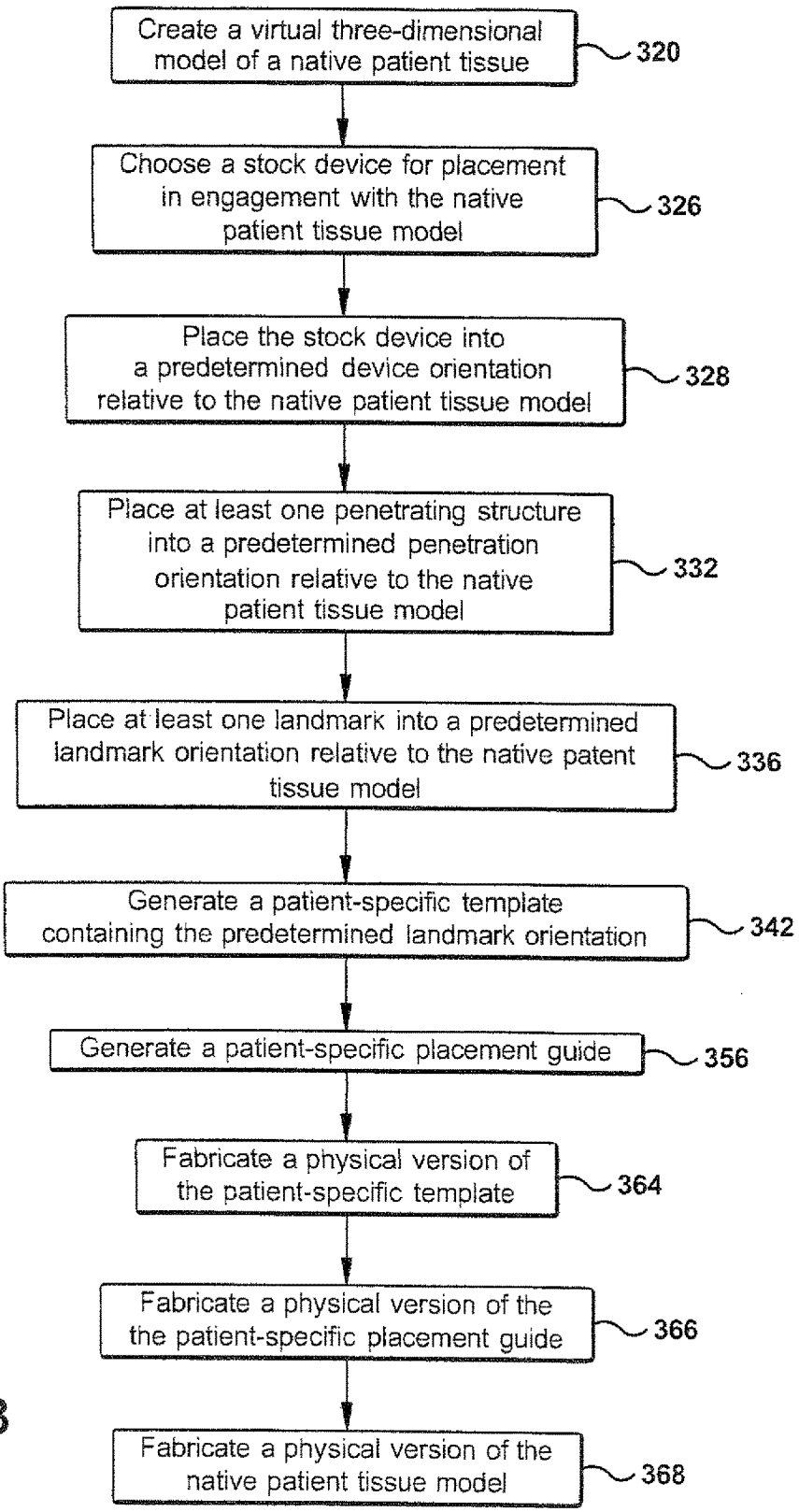
FIG. 3 is a flowchart describing one embodiment of the present invention.

In accordance with the present invention, FIG. 3 is a flowchart depicting one example series of steps of a method of preoperative planning and provision of patient-specific surgical aids. In first action block 320, a virtual three-dimensional model of a native patient tissue is created. A "native" patient tissue herein is used to reference the status of the actual, physical patient tissue at the time that the surgery is being planned. For example, the native patient tissue may have been in the "native" state from birth, or may instead be subject to a congenital or acquired deficiency and accordingly be in an altered state as compared to the patient tissue originally present in the patient. Regardless of the mechanism by which the patient tissue came into the "native" condition, the "native" patient tissue is used herein to reference the expected state of the patient tissue at the time of the operation—when the user cuts into the patient's body, the native patient tissue is what will be found at the surgical site.

The virtual model of the native patient tissue may be based upon, for example, scanned image data taken from an imaging scan of the native patient tissue. The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the native patient tissue model may be based upon digital or analog radiography, magnetic resonance imaging, or any other suitable imaging means. The patient tissue model will generally be displayed for the user to review and manipulate preoperatively, such as through the use of a computer or other graphical workstation interface. While this description presumes a three-dimensional model, one of ordinary skill in the art could use a two-dimensional model in a similar manner to that shown and described herein, without harm to the present invention. An example of a virtual model of the native patient tissue is the native patient tissue model 422 shown in FIGS. 4-10.

FIGS. 4-10 pictorially depict the preoperative planning procedure described in the FIG. 3 flowchart. FIGS. 4-10 are example user views of a computer program and/or system for implementing a method of using the present invention, with a perspective view on the left side of each Figure and coronal, sagittal (looking distally from underneath the perspective view, as shown), and transverse views, respectively, from top to bottom on the right side of each Figure.

During preoperative planning with a system such as that described, the user can view the native patient tissue model 422 and, based upon knowledge of other patient characteristics (such as, but not limited to, height, weight, age, and activity level), choose a desired device, described hereafter as a stock device 424, for use in the surgical procedure. This use may include placement in engagement with a native patient tissue model 422, as shown in second action block 326 of FIG. 3. Visually, such as in the user view of FIG. 4, an image of the selected desired stock device 424 may be placed over the native patient tissue model image.

A desired device could be the depicted stock prosthetic implant, a custom prosthetic implant, a stock or custom instrument (not shown), or any other desired item. Because three-dimensional image models are available of many instruments and prosthetic implants, whether stock or custom, the user may be able to "install" the instrument or prosthetic implant virtually in the native patient tissue model 422 via the preoperative computer simulation described herein. During such a simulation, the user can automatically and/or manually adjust or reorient the position of the virtual stock device 424 with respect to the virtual native patient tissue model 422, even to the extent of simulating the dynamic interaction between the two, as may be helpful to refine the selection, placement, and orientation of the stock device for a desired patient outcome. The stock device 422 may be chosen from a library of available stock devices, with the choice based upon any factor or characteristic desired.

The term "stock" is used herein to indicate that the component indicated is not custom-manufactured or -configured for the patient, but is instead provided as a standard inventory item by a manufacturer. A particular stock component may be selected automatically by the system and/or manually by the user from a product line range (e.g., the aforementioned library) of available components, optionally with the user specifying a desired configuration, general or particular size (e.g., small, medium, large, or a specific measurement), material, or any other characteristic of the component. Indeed, the stock component could be manufactured only after the user has selected the desired options from the range of choices available. However, the stock component is differentiated from a custom-manufactured or bespoke component in that the stock component is agnostic and indifferent regarding a particular patient anatomy during the design and manufacturing processes for an instrument, prosthetic implant, or other component intended for that patient, while the patient anatomy is an input into at least one design and/or manufacturing process for a custom-manufactured component. The following description presumes the use of a stock prosthetic implant and stock instrument, though one of ordinary skill in the art will be able to provide for the use of the present invention with a custom-manufactured prosthetic implant or instrument, instead.

Figure 4:
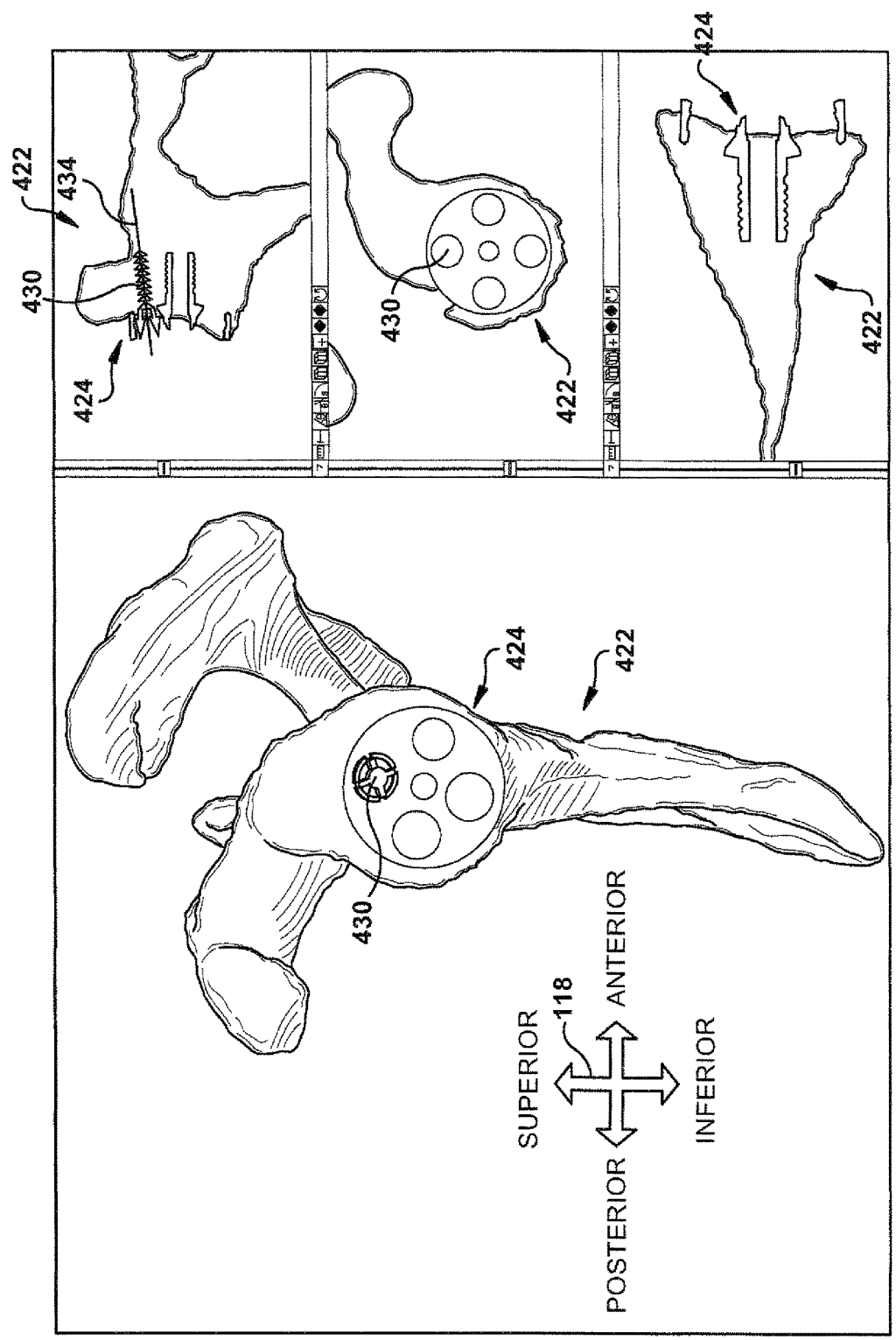
FIGS. 4-10 are example user views of a program for generating the embodiment of FIG. 3.

At third action block 328 of FIG. 3, the stock device 424 is placed, or reoriented, into a predetermined device orientation relative to the native patient tissue model 422, to achieve the position shown in FIG. 4. An orientation of a structure, as used herein, includes both the absolute location of the structure upon or with respect to another structure and the arrangement or positioning in space of the structure (e.g., rotation, pitch, yaw, camber, or any other placement-related variable of the structure).

The system may place the stock device 424 into the predetermined device orientation automatically by the system and/or manually by the user, based upon any suitable criteria. For example, the system may provide at least two optional device orientations and compare the optional device orientations to each other based upon any desired device property(ies), in a weighted or unweighted manner. Device properties that could factor into the comparison include at least one of device size, device shape, device material, number of fasteners to be used, type of fasteners, size of fasteners, shape of fasteners, amount of patient tissue alteration, type of patient tissue alteration, orientation of the stock device relative to another stock device (e.g., orientation of one part of a prosthetic joint relative to another part of the prosthetic joint which has already been [virtually] placed with respect to the native patient tissue model), and physical quality of the native patient tissue. A plurality of optional device orientations could be compared to one another based on these or any other suitable factors, in any suitable manner (e.g., using a decision algorithm or comparison scheme). It is contemplated that certain device properties may be more important than others, and that the comparisons will be made automatically by the system and/or manually by the user to allow for compromises—if needed—on certain device properties in order to strive for a better overall outcome.

Once the comparison(s) is (are) made, the user and/or system chooses an optional device orientation based upon the comparison and designates the chosen optional device orientation as the predetermined device orientation. The predetermined device orientation of the stock device 424 with respect to the native patient tissue model 422 is shown in the FIG. 4 view. As is especially apparent in the coronal (top right) and transverse (bottom right) portions of FIG. 4, there may be some overlap or superposition between the stock device 424 and the native patient tissue model 422. This superposition is permissible in the virtual environment of the described system and may helps to indicate areas of the native patient tissue model 422 which could be targeted for alteration during placement of the stock device 424.

Once a chosen stock device 424 has been virtually placed in a desired orientation with respect to the native patient tissue model 422 (it will be understood that some mechanical modification might need to be made to the actual native patient tissue to accomplish this implant placement in situ), the placement of any fasteners or other penetrating structures 430 (e.g., a drill, guide pin, or other surgical tool), when present, may also be planned through the use of the computer simulation. Consideration of the location, amount, and pathology of the patient tissue, any of the above device properties, or any other desired factors, may be taken into account in this optional penetrating structure 430 planning. The penetrating structure(s) 430 may be chosen from a library of available penetrating structures.

Manually and/or with automatic computer assistance, the user can experiment with various fastener sizes, placements, and orientations for securing the stock prosthetic implant to the patient tissue, and/or with various other types of penetrating structure 430 insertions into the native patient tissue model 422 similarly to the previously described device placement, until reaching at least one predetermined penetration orientation (such as that shown in FIG. 4) for at least one penetrating structure(s) 430 to be used with the surgical procedure being planned, as described in fourth action block 332 of the FIG. 3 flowchart. When the penetrating structure 430 positioning has been finalized, with the stock device 424 virtually positioned in a predetermined device orientation with respect to the patient tissue, a location and target trajectory 434 may be defined for each of the penetrating structures 430 present (if any) to follow during installation.

The term "trajectory" is used herein to indicate an invisible line along which an elongate body will travel to reach the predetermined penetration orientation.

Once the predetermined device orientation and any desired predetermined penetration orientation(s), when present, are known, the displayed images of the selected stock device 424 and/or of any included penetrating structures 430 may be removed from the displayed image of the native patient tissue model 422, for greater clarity in following portion(s) of the preoperative planning system. The displayed images of the selected stock device 424 and/or of any included penetrating structures 430 may be reinstated and re-removed, as desired, during any phase of the below operations.

Figure 5:
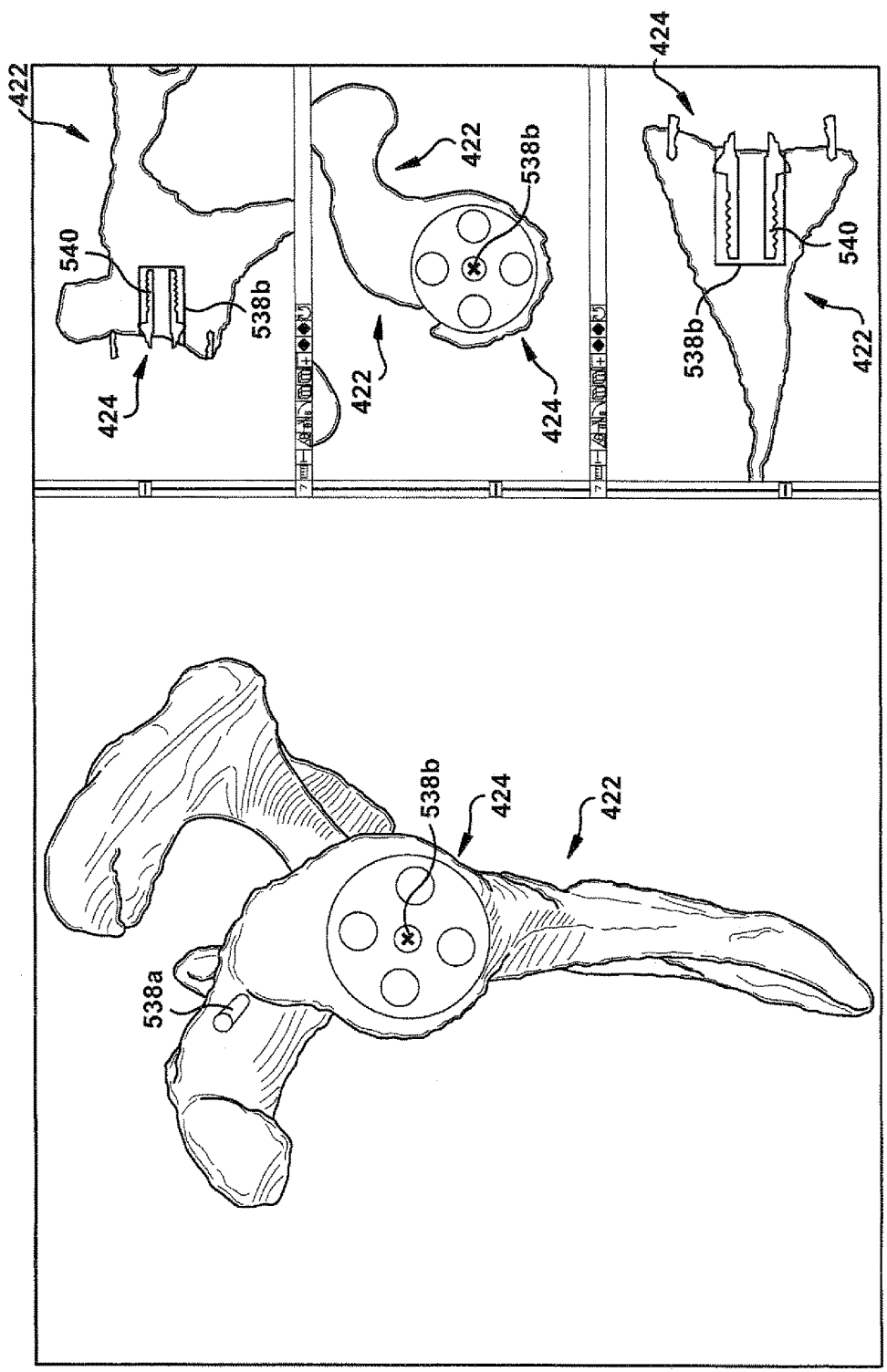

As shown in fifth action block 336 of FIG. 3, at least one landmark 538 (shown in FIG. 5) may be placed in at least one predetermined landmark orientation relative to the native patient tissue model 422. The landmark(s) 538, when present, represent a chosen point in space and/or indicate a chosen direction/orientation relative to the native patient tissue model 422 and are used to convey positional information to the user during a surgical procedure. For example, a guide pin is displayed as a three-dimensional landmark 538a spaced apart from the stock device 424 over the image of the native patient tissue model 422 in FIG. 5, while an aperture or cavity formed in the native patient tissue model is shown as a two-dimensional landmark 538b (i.e., represented by a cross mark when seen from above or below) corresponding to a central portion of the stock device in FIG. 5. In fact, the "negative" aperture-type landmark 538b of FIG. 5 is configured to receive a device shaft 540 of the stock device 424, which helps to locate and stabilize the stock device with respect to the native patient tissue model 422. One of ordinary skill in the art would readily be able to instead provide a "positive" pin- or shaft-type landmark (not shown) protruding from the native patient tissue model 422 and adapted to be received in a cavity (not shown) of another type of device, in an axle-type manner.

Regardless of the number, location, type, or any other characteristics of the provided landmark(s) 538, it is contemplated that the user will want to transfer the landmarked information to the actual patient tissue during the surgical procedure. To that end, a patient-specific template may be created using the system described herein. The landmark 538 could also or instead be placed during the surgical procedure using a robotic surgical aid, adjustable reusable (e.g., "dial-in") tools, intraoperative imaging, or any other suitable placement aid.

Figure 6:
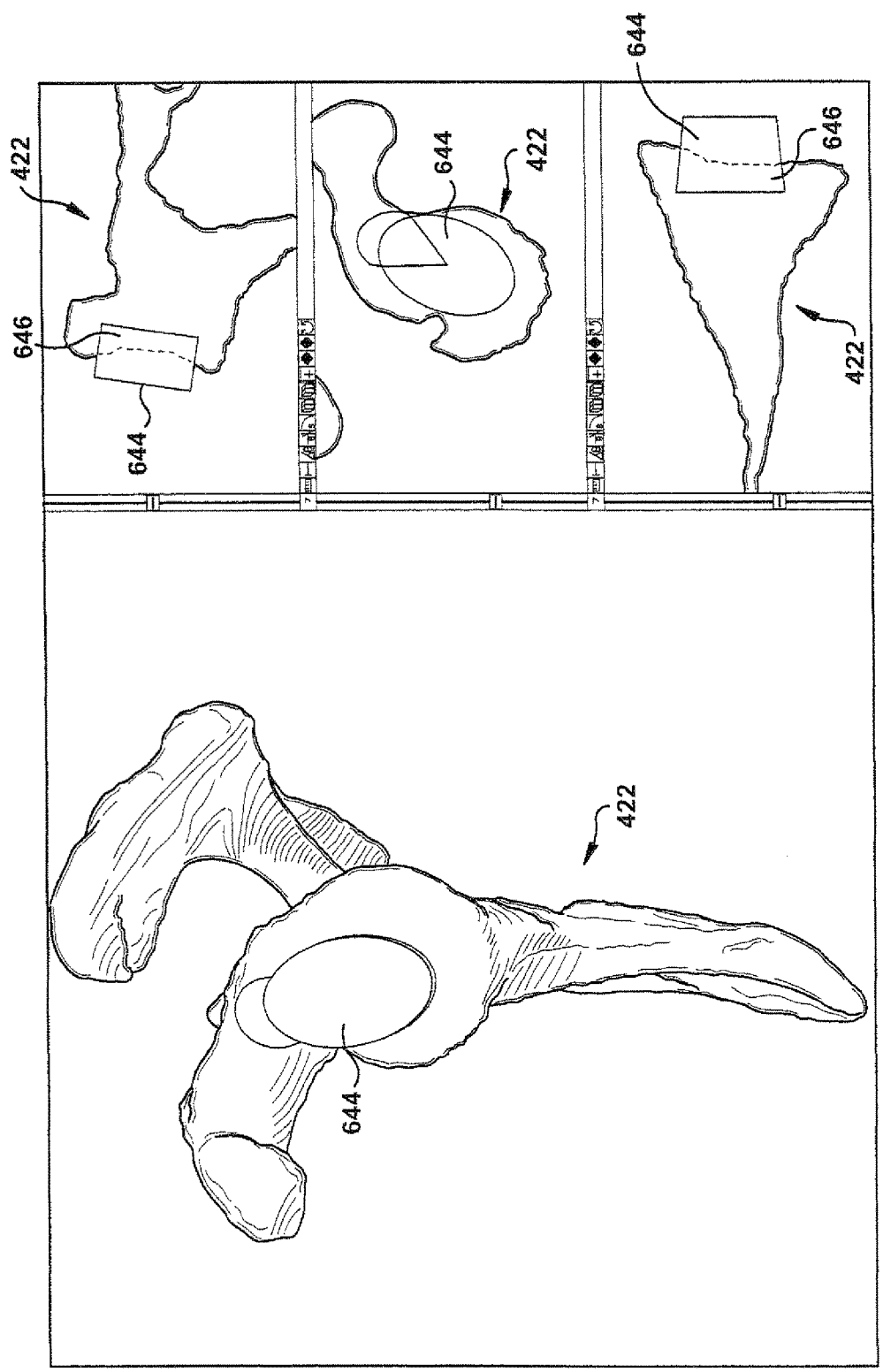
Figure 7:
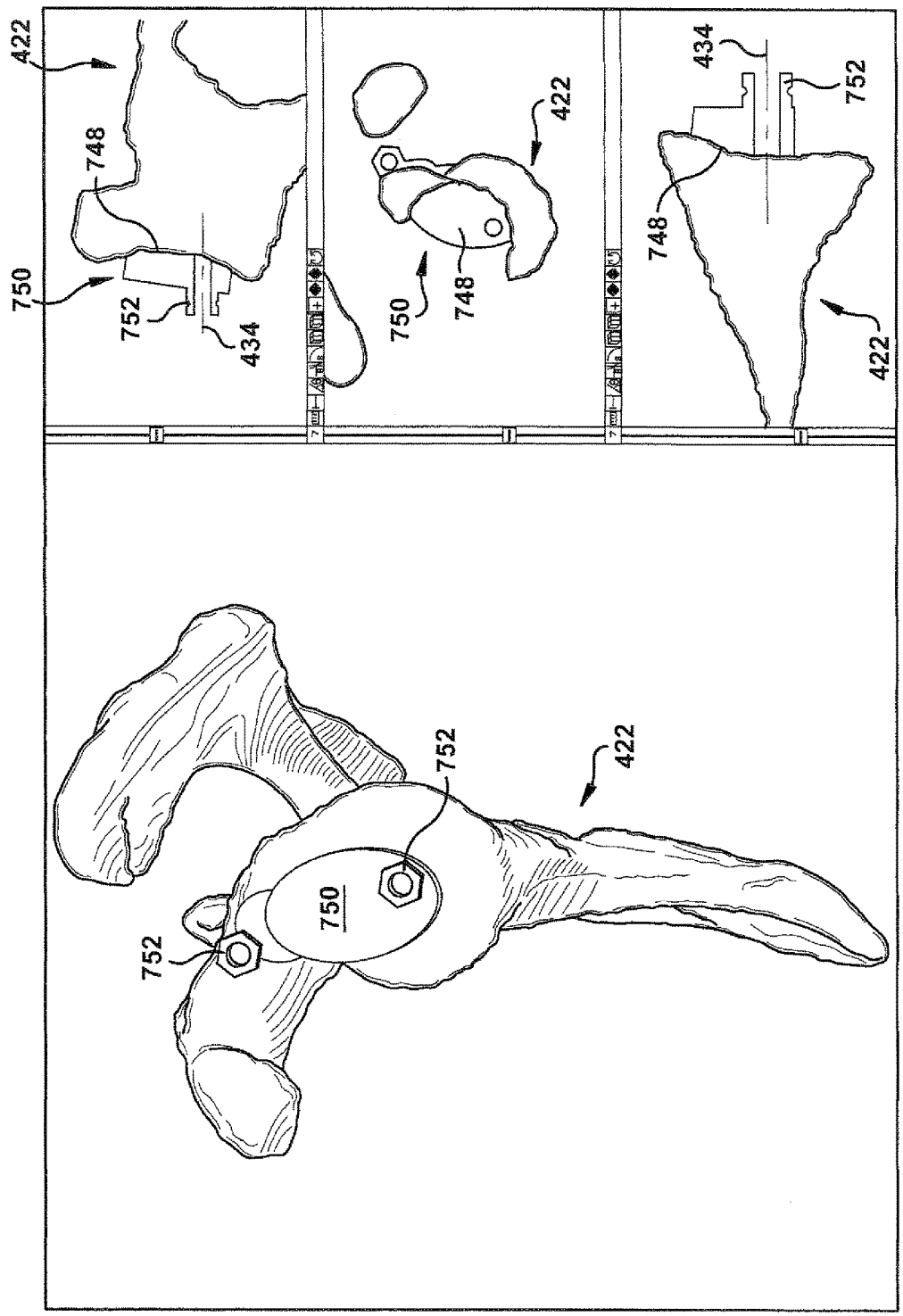
Figure 8:
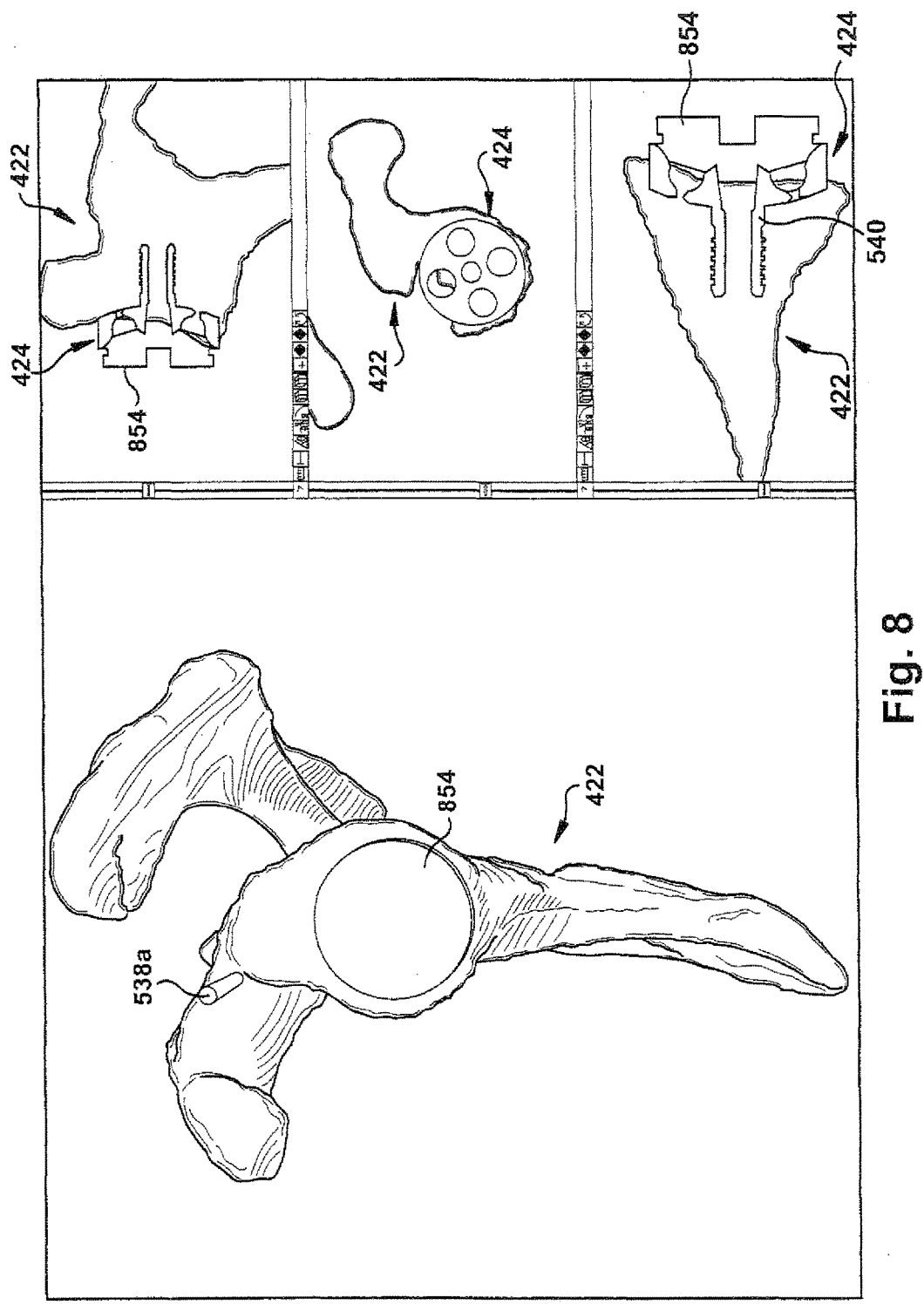

As shown at sixth action block 342 of FIG. 3, a patient-specific template is generated, which may be accomplished by the system with steps represented in user views such as the sequence of FIGS. 6-7. As shown in FIG. 6, a template blank 644 is placed into a desired (final) predetermined template orientation with respect to the native patient tissue model 422. The template blank 644 may be selected, automatically and/or manually, from a library of available template blanks and may be placed, again automatically and/or manually, into the predetermined template orientation based upon any of the above device properties or any other desired factors.

As is particularly apparent in the coronal (top right) and transverse (bottom right) portions of FIG. 6, at least a portion of the native patient tissue model 422 and at least a portion of the template blank 644 (virtually) overlap to create a superposed volume 646 of space which is occupied by both the native patient tissue model and the template blank. Since this superposed volume 646 is impracticable during the actual physical surgical procedure, the superposed volume 646 is (again, virtually) removed from the template blank 644 to create a mating surface 748 of the template blank adjacent the native patient tissue model 422. In other words, the system adjusts the dimensions of the bottom template surface 748 to mate with a surface of the native patient tissue model 422. The term "mate" is used herein to indicate a relationship in which the contours of two structures are at least partially matched or coordinated in at least two dimensions.

The mating surface 748 may be seen in particularly the coronal (top right) and transverse (bottom right) portions of FIG. 7. The patient-specific template 750 may be, for example, the type disclosed in co-pending U.S. Provisional Patent Application No. 61/408,359, filed 29 Oct. 2010 and titled "System and Method for Association of a Guiding Aid with a Patient Tissue", the entire contents of which are incorporated herein by reference.

Regardless of its nature, the patient-specific template 750 virtually contains or embodies at least one predetermined landmark orientation and has at least one landmark guiding feature 752 configured to place a landmark 538 in the predetermined landmark orientation when the patient-specific template 750 is mated with the native tissue model 422. As shown in FIG. 7, at least one landmark guiding feature 752 is an aperture through the patient-specific template 750 which is configured to guide a penetrating structure, such as a guide pin or drill bit, into the native patient tissue model 422 at a predetermined penetration location and with a specified target trajectory 434.

When the landmark 538 is a two-dimensional landmark such as a marking on the surface of the native patient tissue, the target trajectory 434 of the landmark guiding feature 752 will likely be of little to no import. In contrast, when the landmark 538 is a three-dimensional landmark such as a drilled hole or an elongate guide pin, the target trajectory 434 of the landmark may bear some significance. In FIG. 7, the depicted target trajectory 434 corresponds to a desired drilling trajectory for an aperture which receives a device shaft 540 at a later stage of the surgical procedure. In this sense, therefore, at least one of the landmark guiding features 752 shown in FIG. 7 may also serve as a penetration-guiding feature.

Once the landmark(s) 538 have been virtually placed into the predetermined landmark orientation(s) at fifth action block 336 of FIG. 3 and the patient-specific template 750 created at sixth action block 342, the stock device 424 may be (virtually) re-placed upon the native patient tissue model 422 and at least one patient-specific placement guide 958 may be generated at seventh action block 356 of FIG. 3. The patient-specific placement guide 958 may be configured to interact simultaneously with at least one previously placed landmark (here, at least guide pin-type landmark 538a) and with the stock device 424 when the stock device is in the predetermined device orientation.

The patient-specific placement guide 958 may be, for example, similar to any of those disclosed in co-pending U.S. Provisional Patent Application No. 61/408,324, filed 29 Oct. 2010 and titled "System and Method for Assisting with Attachment of a Stock Implant to a Patient Tissue", or in co-pending U.S. Provisional Patent Application No. 61/408,376, filed 29 Oct. 2010 and titled "System and Method for Assisting with Attachment of a Stock Instrument to a Patient Tissue", the entire contents of both of which are incorporated herein by reference.

Regardless of the type of patient-specific placement guide 958 provided, the patient-specific placement guide may be generated similarly to the patient-specific template 750. Namely, a placement guide blank 854, shown in FIG. 8, may be automatically or manually selected, optionally from a library of available placement guide blanks. It is contemplated that the placement guide blank 356 may be selected responsive to the selection of the stock device 424, because in many applications of the present invention, the patient-specific placement guide 958 will nest into or mate with some physical feature of the stock device. For example, and as shown in particularly the transverse view of FIG. 8, the placement guide blank 356 may nest with a portion of the stock device 424 substantially collinear with the device shaft 540 to help positively locate the patient-specific placement guide with respect to the stock device.

Figure 9:
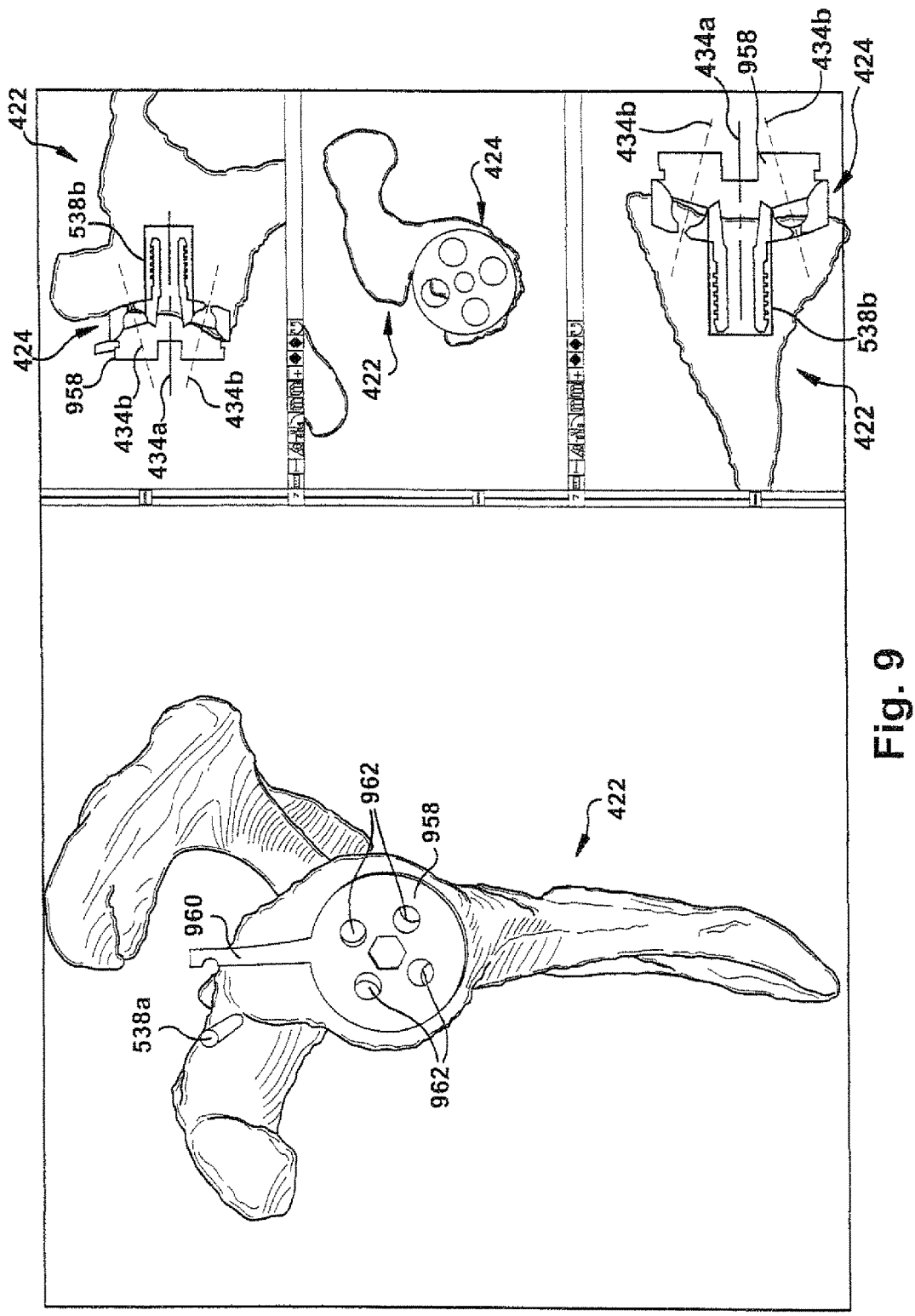

The placement guide blank 854, once selected by any suitable procedure, may then be (virtually) altered to register with at least one landmark 538, as shown in FIG. 9 when the patient-specific placement guide 958 is mated with the stock device 424 and the stock device is in the predetermined device orientation. Registration of the patient-specific placement guide 958 with a chosen landmark 538 helps to indicate that the stock device 424 has achieved the predetermined device orientation when the patient-specific placement guide 958 is mated or nested with the stock device and the stock device is in contact with the native patient tissue model. The term "register" or "registration" is used herein to indicate a predetermined condition of correct alignment or proper relative position between a landmark 538 (of any type) and some feature of the structure (here, the patient-specific placement guide 958) being registered. For example, when the landmark 538 is a two-dimensional marking on the native patient tissue model 422, the registration might occur when an inscribed mark on the patient-specific placement guide 958 aligns with the two-dimensional landmark.

As another example, and as shown in FIG. 9, the landmark 538a might be a three-dimensional landmark such as a guide pin. In this instance, the patient-specific placement guide 958 includes at least one orienting feature 960 (having previously been provided to the guide blank) which will register with the selected landmark 538a by contact with the guide pin embodying that landmark when the patient-specific placement guide 958 is mated or nested with the stock device 424 (as shown in FIG. 9) and the stock device is in contact with the native patient tissue model in the predetermined device orientation. In the view of FIG. 9, the stock device 424 is not yet in the predetermined device orientation as indicated by the separation of the orienting feature 960 and the landmark 538a, though the patient-specific placement guide 958 is mated with the stock device, as can be seen in particularly the coronal and transverse views of FIG. 9.

In addition to the guiding/orienting function provided by the patient-specific placement guide 958, at least one penetration-guiding feature 962 (four shown in FIG. 9) may be provided by the patient-specific placement guide. Here, the target trajectory 434a indicates a target trajectory and associated penetration location associated with a landmark 538b, whereas the target trajectories marked 434b (shown in dashed line in the coronal and transverse views since not strictly present in those sections) and the associated penetration locations in FIG. 9 are associated with one or more penetrating structures (not shown in FIG. 9), such as fasteners, drill bits, other surgical tools, or any other components used in the surgical procedure which the user wishes to guide with the assistance of the patient-specific placement guide 958.

FIG. 10 is similar to FIG. 9, though the stock device 424 has been reoriented into the predetermined device orientation, as indicated by the registration of the orienting feature 960 and the landmark 538a. As can also been seen in FIG. 10, the body of the patient-specific placement guide 958 has been rotated sufficiently to bring the penetration-guiding features 962 into a different rotational orientation with respect to the native patient tissue model 422 than that of FIG. 9. The target trajectories 434b of the penetration-guiding features 962 should be in the desired penetration locations with respect to the native patient tissue model 422 when the stock device 424 has been brought into the predetermined device orientation.

Once the patient-specific template 750 and/or the patient-specific placement guide 958 have been generated as desired, including any desired features as described above, a physical version of the patient-specific template (when desired) is created at eighth action block 364 of FIG. 3 and a physical version of the patient-specific placement guide (when desired) is created at ninth action block 366 of FIG. 3. These physical versions of the patient-specific template 750 and/or the patient-specific placement guide 958 are tangible (e.g., material and palpable) representations of the virtual versions of the corresponding items as manipulated, adjusted, and otherwise created using a system similar to that shown via the user views of FIGS. 4-10.

Optionally, and as shown in tenth action block 368 of FIG. 3, a physical three-dimensional version of the native patient tissue model 422 may be fabricated as a tangible (e.g., material and palpable) representation of the virtual version of the native patient tissue model. This physical native patient tissue model, sometimes referred to as a "surrogate model" for its usefulness to the surgeon as a manipulable surrogate of the actual patient tissue, will be discussed in detail below, with reference to FIGS. 16A-26D.

The patient's name, identification number, surgeon's name, and/or any other desired identifier may be molded into, printed on, attached to, or otherwise associated with the physical version(s) of the patient-specific template 750, the patient-specific placement guide 958, and/or the native patient tissue model 422 in a legible manner. The tangible representations of the patient-specific template 750, the patient-specific placement guide 958, and/or the native patient tissue model 422 may be made by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process.

Once the physical versions of the patient-specific template 750, the patient-specific placement guide 958, and/or the native patient tissue model 422 have been manufactured and prepared for use (e.g., mechanically or chemically cleaned, cured, sterilized, or the like) using any suitable process(es), they are available for use during surgical procedures as described above and in the incorporated references.

The preoperative planning system disclosed herein allows the user to experiment with different placements and selections of stock devices 424 and/or custom or patient-specific components in an effort to produce positive patient outcomes. FIGS. 11A-14B depict various examples of steps, alternate options, and considerations that one of ordinary skill in the art may find useful in preoperative planning, particularly with respect to selection of the stock device 424 and of the predetermined device orientation.

Figure 11B:
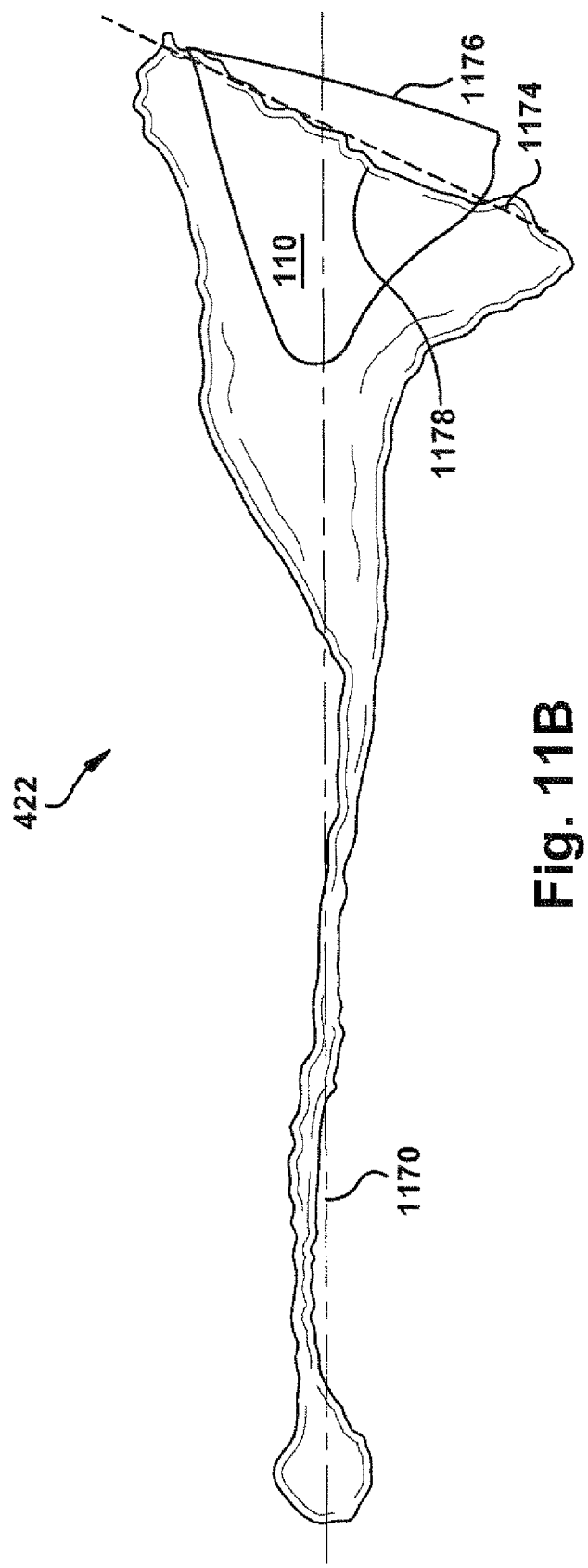

FIGS. 11A-11B depict a transverse view of a native patient tissue model 422 of a typical clinical case of a patient with osteoarthritis, having moderate bone loss. The scapular plane 1170 is perpendicular to reference plane 1172. The reference plane also represents the 0° reference from which glenoid version is measured. The lower portion of FIGS. 11A-11B is posterior and the top portion of these Figures is anterior, as shown by direction arrow 118'. The diagonal dashed line labeled 1174 represents the native glenoid plane of the patient. In this case, the native glenoid plane 1174 exhibits a retroversion angle of approximately 26° from the reference plane 1172. Glenoid version in the normal population is reported to commonly be between 5° of anteversion and 15° of retroversion. The average normal glenoid version is approximately 1-2° of retroversion.

The goal of arthroplasty surgery is to correct pathologic anatomy and restore as best as possible normal anatomy and function. Corrective options range between placing an implant component at the standard ideal of perpendicular to the plane of the scapula (0°) up to the pathologic version (in this case, 26° of retroversion). Common practice today is usually to correct version with an attempt to place a stock device 424 approximately perpendicular to the scapular plane 1170 (i.e., lying along the reference plane 1172 at about 0° of version). For clarity of description, the "angle" of the stock device 424 is referenced hereafter as being the angle measured from a top face of the stock device, the top face being foremost in the perspective view of FIG. 4.

There normally will be a secondary surgical goals to minimize removal of patient tissue needed to accommodate the stock device 424, seat the entire stock device on the prepared patient tissue surface, and minimize unwanted perforation of the outer walls of the glenoid vault 110 or other patient tissue by the device shaft 540 or another penetrating structure 430 used in the surgical procedure or remaining in the patient tissue postoperatively. When formulating a preoperative plan, typical items of concern include the bone (or other patient tissue) loss in the patient, the position and orientation of the normal joint line, and where the stock device 424 or other component should be placed to aim toward a positive patient outcome.

The present inventors have found that an average patient tissue model 1176 (e.g., a "vault model") may be useful in tailoring a surgical procedure to fit the needs of an individual patient. A suitable average patient tissue model 1176 is described in co-pending U.S. patent application Ser. No. 12/043,634, filed 6 Mar. 2008, and titled "Method and Apparatus for Preparing for a Surgical Procedure", the contents of which are hereby incorporated by reference in their entirety. In a similar manner, the shape of an average acetabular vault may be used as a suitable average patient tissue model and have some clinical relevance when defining the normal anatomic relationships from the pathologic anatomy in a hip use environment. The average patient tissue model 1176 of a glenoid vault 110 is shown superimposed on the native patient tissue model 422 in FIG. 11B. Although this is an "average" view, the contours of the average patient tissue model 1176 can be seen to substantially mirror the contours of the native glenoid vault 110 of even the depicted pathologic scapula 100.

FIG. 11B is similar to FIG. 11A, with the addition of an average patient tissue model 1176. The average patient tissue model 1176 helps to define the location of the normal joint line and the version of the normal glenoid fossa 1178 in a patient-specific manner. The average patient tissue model 1176 may help define reconstruction goals in pathologic cases, and may assist with selection of position and type of a stock device 424 or a custom device (not shown). Selection of version for the stock device 424 may be at least partially dependent upon the version of the average patient tissue model 1176 which defines patient-specific normal anatomy. In the patient of FIGS. 11A-14B, normal patient version, based upon the average patient tissue model 1176, may be seen to be approximately 12° of retroversion, as shown by the angle of the rightmost face (in the orientation of the Figures) of the average patient tissue model 1176 with respect to reference plane 1172.

When planning a surgical procedure using preoperative imaging, the user may specify at least one structural change to the native patient tissue to facilitate placement of a stock device in a predetermined device orientation. For example, native patient tissue could be drilled, planed, reamed or otherwise removed, or the native patient tissue could be built up using bone grafts or other substances, with the latter being much more difficult to do than the former during a standard surgical procedure. Using the system described above, a (virtual) altered patient tissue model (not shown) can be generated and viewed or otherwise used in the preoperative planning. Optionally, a physical three-dimensional version of the altered patient tissue model may be fabricated as a tangible representation of the virtual version of the altered patient tissue model. When provided, the physical altered patient tissue model may also include at least one information feature providing clinically useful information to the user. For example, a landmark 538 (e.g., a cavity or aperture) may be present in the physical altered patient tissue model and may therefore be made palpable or otherwise apparent to the user during the surgical procedure. The physical altered patient tissue model, when present, may be used and referenced similarly to the aforementioned physical native patient tissue model.

Figure 12A:
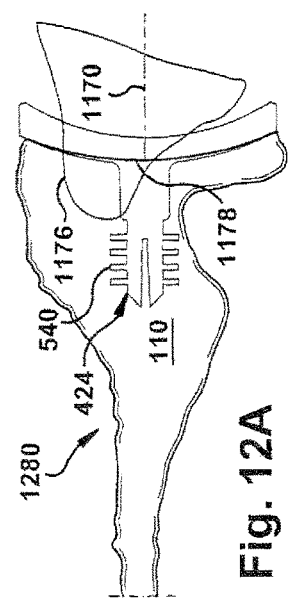
FIGS. 12A-12C are schematic views depicting placement options for one element of the embodiment of FIG. 3 in a first configuration.

FIGS. 12A-14B are partial transverse cross-sectional schematic views of a scapula which depict a comparison of the likely surgical outcomes for various preoperative planning options. FIGS. 12A-14B depict various ways in which the native patient tissue model 422 can be compared to a reference patient tissue model (regardless of whether any alterations are made to the native patient tissue model), and the effect of that comparison on the predetermined device orientation. The predetermined device orientation can be adjusted, automatically by the system and/or manually by the user, responsive to the comparison of the native patient tissue model 422 to the reference patient tissue model. The reference patient tissue may be at least one of a (mirrored) image of a contralateral patient tissue of the same or a different patient, a value taken from a standard reference patient tissue, a value range taken from a standard reference patient tissue, and the aforementioned average patient tissue model 1176. In FIGS. 12A-14B, the reference patient tissue is shown and described as being the average patient tissue model 1176. In FIG. 12A, a stock device 424 has been superimposed upon the native patient tissue model 422 of FIGS. 11A-11B in a version of 0° from the coronal plane (shown in FIGS. 11A-13C as scapular plane 1170), with the bottom portion (in the orientation of FIGS. 11A-13C) of the stock device being located on an outer surface of the native patient tissue. Since FIGS. 12A-13C show the scapula 100 having portions of the native tissue removed to accommodate each stock device 424, the patient tissue shown can be described as an altered patient tissue model 1280. The excision of fairly large amounts of native patient tissue is likely to adversely affect the dynamics within the shoulder joint. Additionally, the glenoid vault 110 may be shaved down enough that the device shaft 540 is in danger of breaching the glenoid vault wall, which is generally undesirable and can cause patient discomfort and possibly result in undesirable reoperation. Accordingly, one goal of a pre-surgical planning process using the average patient tissue model 1176 is to attempt to replicate the total volume (or area, as depicted in the cross-sectional views of FIGS. 12A-14B) of the average patient tissue model 1176 with a combination of the total volume (or area) of the altered patient tissue model 1280 and the stock device 424.

It is apparent from FIG. 12A that a substantial amount of the native patient tissue will have to be removed from the native patient tissue model 422 to allow the stock device 424 to seat firmly and maintain the 0° version with the stock device 424 substantially centered, posteriorly to anteriorly, upon the glenoid fossa 1178. The device shaft 540 in FIG. 12A is in danger of breaching the glenoid vault 110 wall, which should be avoided.

Figure 12B:
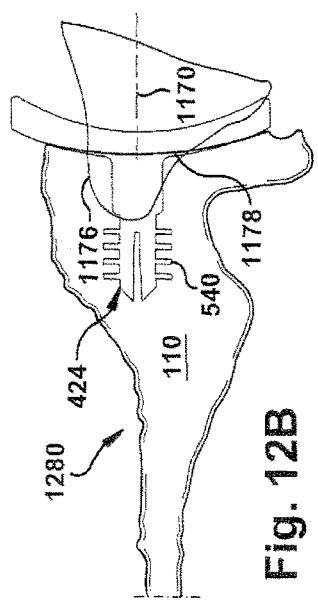

FIG. 12B also shows an altered patient tissue model 1280 with a relatively large volume of native patient tissue removed, though less removed than in FIG. 12A. In FIG. 12B, the version is still corrected to 0° from the reference plane 1172, but the stock device 424 has been moved upward (in the orientation of the Figures) to distance the device shaft 540 from the glenoid vault 110 wall. This shifting of the stock device 424 can be seen to have a different adverse effect, however—namely, the stock device now substantially overhangs the anterior edge of the glenoid fossa 1178.

This problematic 0° version correction is an example of a value taken from a standard reference patient tissue—many users will routinely correct version in all such cases to 0° as shown. As an example of a value range taken from a standard reference patient tissue, the version may be corrected to a value taken from the range of −5° to +5°, with the user's experience and intuition leading to the selection of one value from that range. Another example, in a hip standard reference patient tissue, might prescribe a range of 10-30° of anteversion and 30-55° of abduction for an acetabular prosthetic implantation. However, a seemingly reasonable value based upon a standard reference patient tissue—whether for a shoulder, hip, or any other type of surgery—may markedly depart from a value which leads to an acceptable result for a particular patient.

As a result, users will sometimes employ a mirror image of a contralateral native patient tissue (from that patient or another patient) to use as a reference patient tissue. However, even if there is a contralateral native patient tissue to consult (e.g., the patient is not an amputee in that respect), the contralateral native patient tissue may be pathologically or congenitally asymmetrical from even the original state of the native patient tissue which is being surgically corrected. Thus, there is a need for another reference patient tissue for comparison to the native patient tissue model 422.

In the aforementioned co-pending U.S. patent application Ser. No. 12/043,634, filed 6 Mar. 2008, and titled "Method and Apparatus for Preparing for a Surgical Procedure", the average patient tissue model 1176 (i.e., the "vault model") is proposed as providing an appropriate reference patient tissue for a wide range of patients. The average patient tissue model 1176 is shown in FIGS. 12A-13C superimposed over the altered patient tissue model 1280. Accordingly, one of ordinary skill in the art, with reference to the average patient tissue model 1176, will be motivated to preserve more of the native patient tissue by altering the native tissue model 422, and placing the stock device 424 with reference to the average patient tissue model 1176.

Figure 12C:
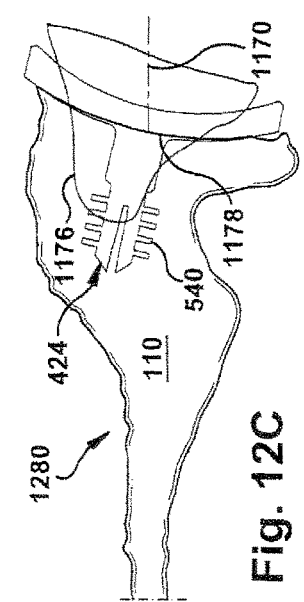

In the situation of FIG. 12C, the average patient tissue model 1176 helps define the native patient joint line and the native version for that particular patient. Accordingly, the average patient tissue model 1176 helps direct the selection of the stock device 424 to restore the native joint line and the patient's native version, thereby reducing the risk of excessive bone removal or perforation of the native patient tissue during or after the stock device is installed. FIG. 12C depicts an altered patient tissue model 1280 with the average patient tissue model 1176 superposed thereupon and the stock device 424 placed according to the average patient tissue model (here, rotated clockwise, in the orientation of the Figures.). It can be seen that placement of the stock device 424 in a patient-specific version (informed by the average patient tissue model 1176) will center the device shaft 420 (posteriorly to anteriorly) in the glenoid vault 110, provide more thorough patient tissue contact for the stock device, and result in less patient tissue removal and greater centering of the stock device on the glenoid fossa 1178 as compared to the 0° versions of FIGS. 12A and 12B. Accordingly, the stock device 424 placement in FIG. 12C would seem to provide a preferred predetermined device orientation compared to the orientations shown in FIGS. 12A and 12B.

Figure 13A:
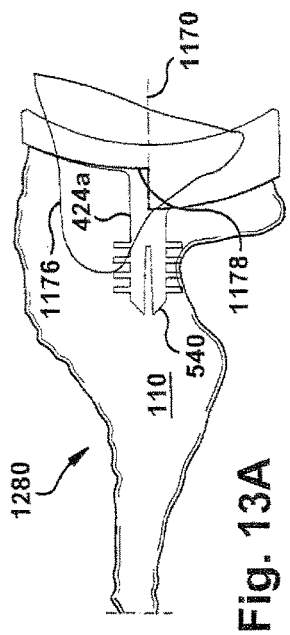
FIGS. 13A-13C are schematic views depicting placement options for one element of the embodiment of FIG. 3 in a second configuration.
Figure 13B:
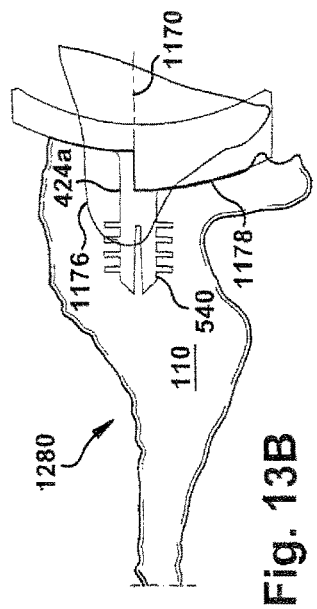
Figure 13C:
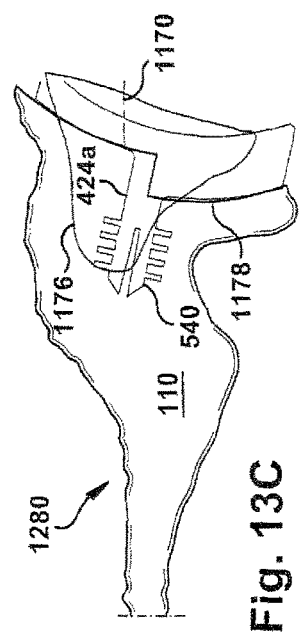

FIGS. 13A-13C depict a similar orientation comparison sequence to that of FIGS. 12A-12C, but including a different stock device 424a than that shown in FIGS. 12A-12C. The stock device 424a includes a thickened leftmost section (in the orientation of the Figures) which helps to compensate for the pathologic state of the native patient tissue. This selection of this stock device 424a, having a second configuration as compared to the first configuration of the stock device 424 of FIGS. 12A-12C allows for the combination of the native glenoid vault 110 plus the stock device 424a to have a similar, and similarly arranged, volume of material as that of the average patient tissue model 1176. The arrangements of FIGS. 13A-13C are analogous to those of FIGS. 12A-12C, excepting the differences in the stock devices 424 and 424a, and therefore the description of FIGS. 12A-12C will not be repeated with respect to 13A-13C.

The views of the combination of the altered glenoid vault 110 plus the stock device 424a of FIGS. 13A-13C may be favorably contrasted with the analogous views of FIGS. 12A-12C, wherein the combination of the altered glenoid vault 110 plus the stock device 424 has a substantially smaller volume in the latter when compared to the average patient tissue model 1176, and thus the latter will have less strength and ability to mechanically perform for the patient as needed for a suitably long time after the surgical procedure. Accordingly, the stock device 424a selection and placement of FIG. 13C appears to meet the goal of preserving native tissue the best of all of the options shown in FIGS. 12A-13C.

Figure 14B:
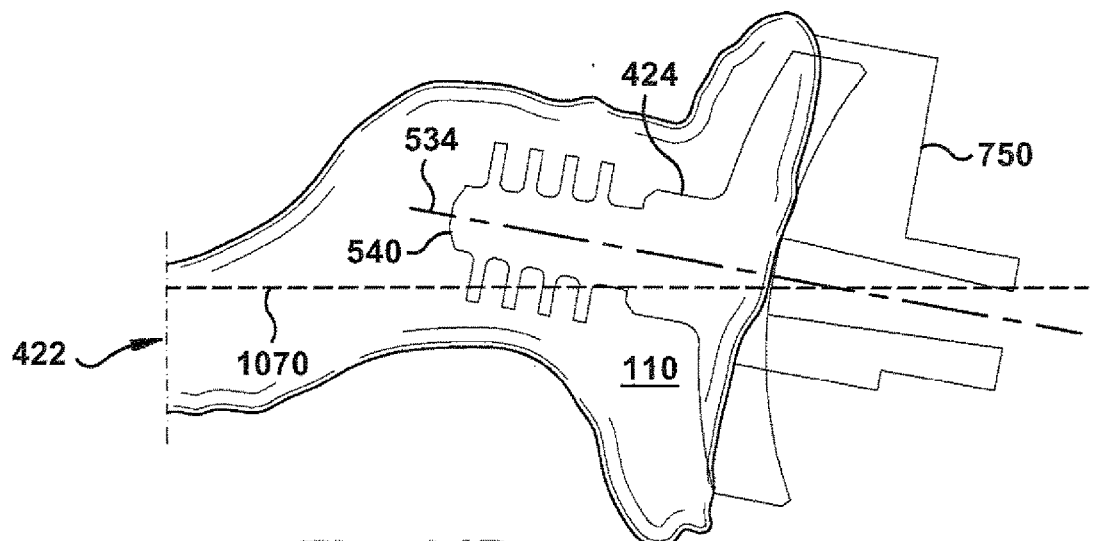
FIGS. 14A-14B are schematic views depicting options for one element of the embodiment of FIG. 3 in the first configuration.
Figure 14A:
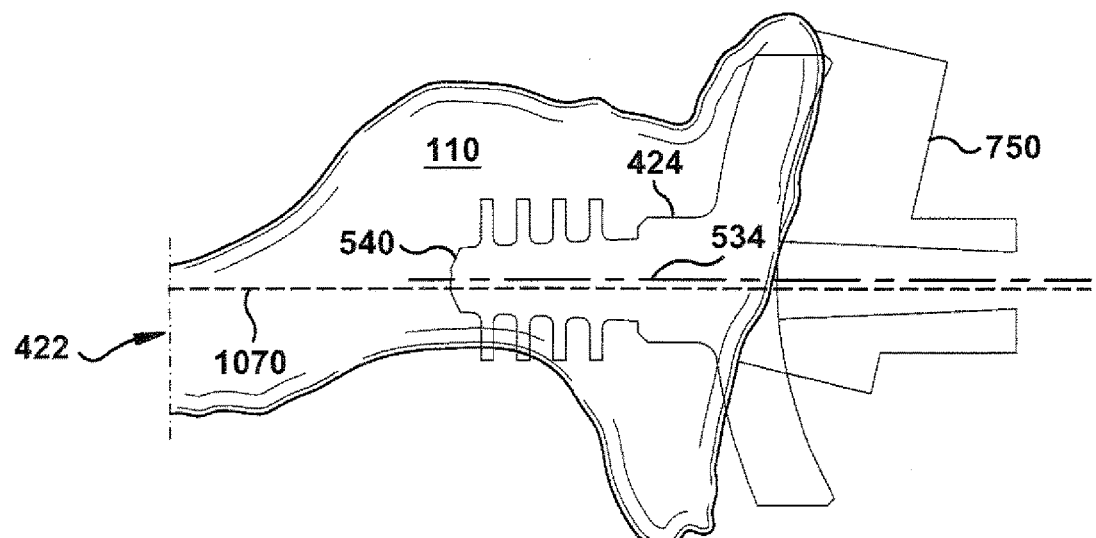

FIGS. 14A-14B show the effects of device orientation upon the native patient tissue model 422. In FIG. 14A, the version has been corrected to 0°. That is, the target trajectory 534 of the patient-specific template 750 is substantially parallel to the scapular plane 1170. As is apparent in FIG. 14A, the device shaft 540 is cutting markedly into the coronal bone of the scapula 100 in an undesirable manner, and a relatively large volume of native patient tissue will need to be removed (near the top of FIG. 14A) to accept the stock device 424. In FIG. 14B, the version has been corrected to a value chosen by the user with consideration of the native patient tissue model 422—the version in FIG. 14B is approximately 12°. As can be seen, by simply tilting the stock device 424 in FIG. 14B as suggested by the average patient tissue model 1176 or by a chosen value out of a value range taken from a standard reference patient tissue, the stock device 424 is seated more securely in the glenoid vault 110, with less removal of native patient tissue required. It will be noted that the patient-specific template 750 shown in FIG. 14A has a target trajectory 534 that is different from the target trajectory embodied in the patient-specific template of FIG. 14B.

Figure 15:
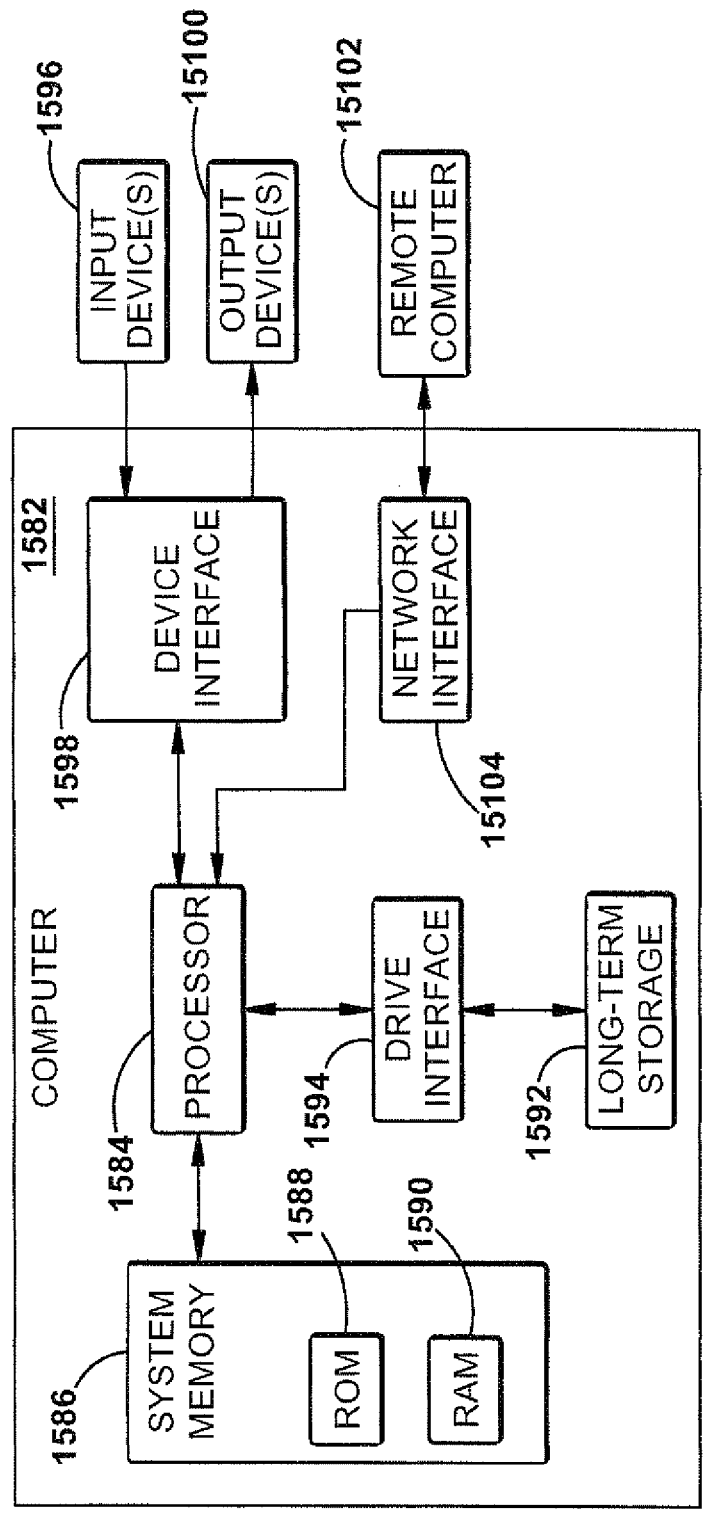
FIG. 15 is a schematic view of a computer system that can be employed to implement systems and methods described herein, such as based on computer executable instructions running on the computer system.

FIG. 15 illustrates a computer system 1582 that can be employed to implement systems and methods described herein, such as based on computer executable instructions running on the computer system. The user may be permitted to preoperatively simulate the planned surgical procedure using the computer system 1582 as desired. The computer system 1582 can be implemented on one or more general purpose networked computer systems, embedded computer systems, routers, switches, server devices, client devices, various intermediate devices/nodes and/or stand alone computer systems. Additionally, the computer system 1582 can be implemented as part of the computer-aided engineering (CAE) tool running computer executable instructions to perform a method as described herein.

The computer system 1582 includes a processor 1584 and a system memory 1586. Dual microprocessors and other multi-processor architectures can also be utilized as the processor 1584. The processor 1584 and system memory 1586 can be coupled by any of several types of bus structures, including a memory bus or memory controller, a peripheral bus, and a local bus using any of a variety of bus architectures. The system memory 1586 includes read only memory (ROM) 1588 and random access memory (RAM) 1590. A basic input/output system (BIOS) can reside in the ROM 1588, generally containing the basic routines that help to transfer information between elements within the computer system 1582, such as a reset or power-up.

The computer system 1582 can include one or more types of long-term data storage 1592, including a hard disk drive, a magnetic disk drive, (e.g., to read from or write to a removable disk), and an optical disk drive, (e.g., for reading a CD-ROM or DVD disk or to read from or write to other optical media). The long-term data storage 1592 can be connected to the processor 1584 by a drive interface 15941594. The long-term data storage 1592 components provide nonvolatile storage of data, data structures, and computer-executable instructions for the computer system 1582. A number of program modules may also be stored in one or more of the drives as well as in the RAM 1590, including an operating system, one or more application programs, other program modules, and program data.

A user may enter commands and information into the computer system 1582 through one or more input devices 1596, such as a keyboard or a pointing device (e.g., a mouse). These and other input devices are often connected to the processor 1584 through a device interface 1598. For example, the input devices can be connected to the system bus by one or more a parallel port, a serial port or a universal serial bus (USB). One or more output device(s) 15100, such as a visual display device or printer, can also be connected to the processor 1584 via the device interface 1598.

The computer system 1582 may operate in a networked environment using logical connections (e.g., a local area network (LAN) or wide area network (WAN) to one or more remote computers 15102. A given remote computer 15102 may be a workstation, a computer system, a router, a peer device or other common network node, and typically includes many or all of the elements described relative to the computer system 1582. The computer system 1582 can communicate with the remote computers 15102 via a network interface 15104, such as a wired or wireless network interface card or modem. In a networked environment, application programs and program data depicted relative to the computer system 1582, or portions thereof, may be stored in memory associated with the remote computers 15102.

It is contemplated that multiple versions of the patient-specific template 750 and/or the patient-specific placement guide 958 could be created during preoperative planning and fabricated as options for the user to select from during the surgical procedure. For example, the user may not be able to clear away surrounding (e.g., soft) tissue from the native patient tissue as well as expected. In this situation, it may be useful to have a patient-specific template 750 with a smaller footprint for easier insertion into the surgical wound and manipulation at the surgical site, even though the smaller footprint means that there is less mating surface 748 to mate with the native patient tissue and provide positive location assistance for the patient-specific template 750.

As mentioned previously, a physical version of the native patient tissue model 422 may be useful to the surgeon before, during, and/or after a surgical procedure. Physical native patient tissue models, or "surrogate models", will now be discussed at length with reference to FIGS. 16A-26D.

Figure 16A:
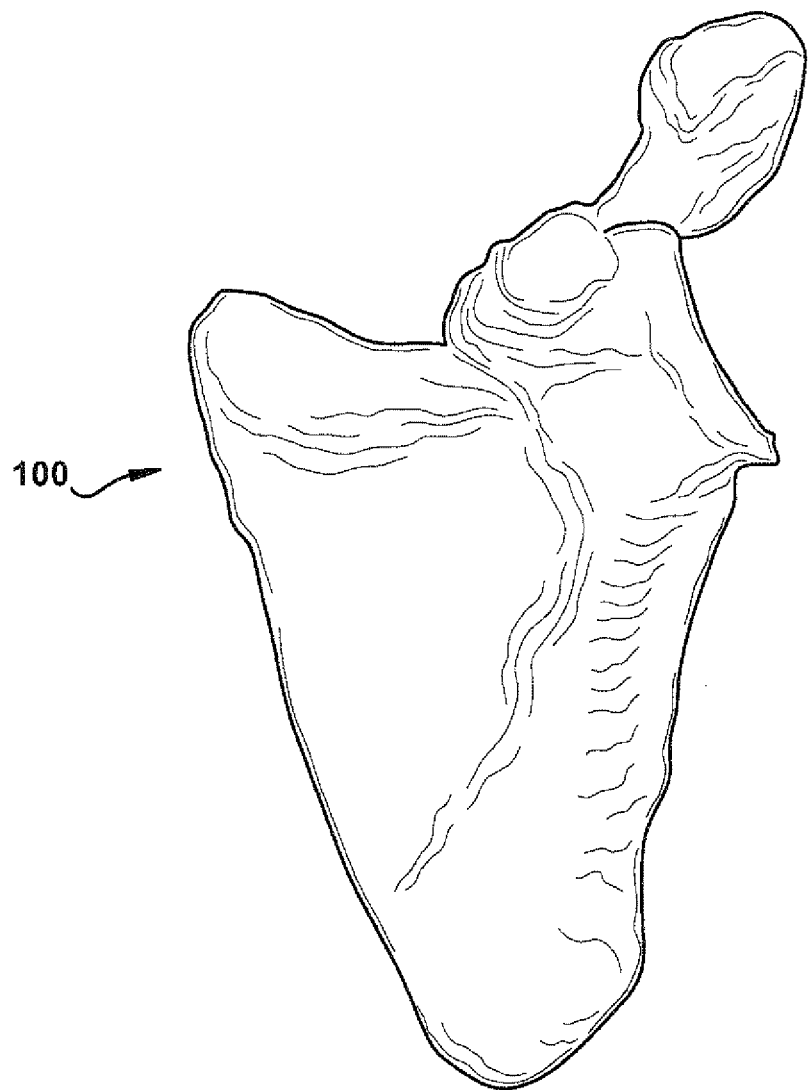
FIGS. 16A-16B are perspective views of a use environment of the present invention.
Figure 16B:
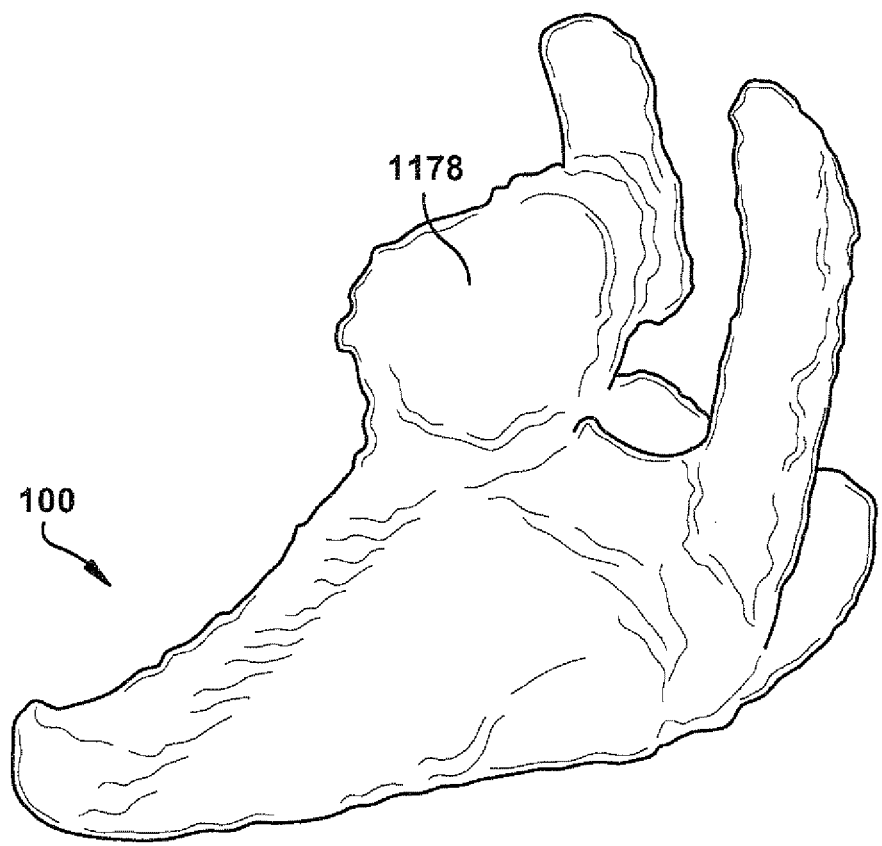

FIGS. 16A and 16B depict different views of a virtual model of a native patient tissue (here a scapula 100). In FIG. 16B, the glenoid fossa 1178 surface is visible. The below description presumes that the present invention is being used to assist with the placement and installation of a glenoid component 216 upon the glenoid fossa 1178. Therefore, the glenoid fossa 1178 can be thought of, in the below description, as a "surface of interest". The term "surface of interest" is used herein to indicate a surface upon/into which a prosthetic device is to be placed or a surface which is to be the main subject of substantially permanent physical modification during a surgical procedure in an effort to provide therapeutic benefit to the patient. "Substantially permanent physical modification" is used here to indicate that the native patient tissue is cut, reamed, drilled, burned, otherwise mechanically or chemically altered, grafted (using natural or synthetic materials), or in any other way physically altered in a manner that remains in situ after completion of the surgery. While another portion of patient tissue other than a surface of interest—whether adjacent to or spaced apart from the surface of interest—may be incidentally physically modified, in either a transient or substantially permanent manner, during the surgical procedure, this incidental modification alone does not transform the other portion of patient tissue into a "surface of interest". As one of a number of possible nonlimiting examples, a "footprint" of bone surface underlying an installed prosthetic device will normally be considered a surface of interest, while examples of patient tissue which have incidental physical modification (temporary or substantially permanent) but would not be considered surfaces of interest in this situation include, but are not limited to, soft tissue adjacent the bone surface which is retracted temporarily for purposes of the procedure, bone surface which is not machined to accept (and/or is not contacted by) the installed prosthetic device, and bone surface which is lightly scored, drilled, or marked for reference purposes during the surgical procedure but which modification does not serve any therapeutic purpose after the surgery is completed. As one of ordinary skill in the art will be aware, a "surface of interest" in most cases will not have clearly defined borders, but that person of ordinary skill in the art will be able to readily differentiate between a surface of interest and another patient tissue, which is not a surface of interest, for a particular application of the present invention.

One of ordinary skill in the art will often be provided with a virtual model of a patient tissue, such as the scapula 100 shown in FIGS. 16A-16B, for preoperative planning use, such as in one of the previously described planning functions. However, a user may find it helpful to have a physical version of the native patient tissue available for pre-operative, interoperative, or even postoperative reference.

Figure 17A:
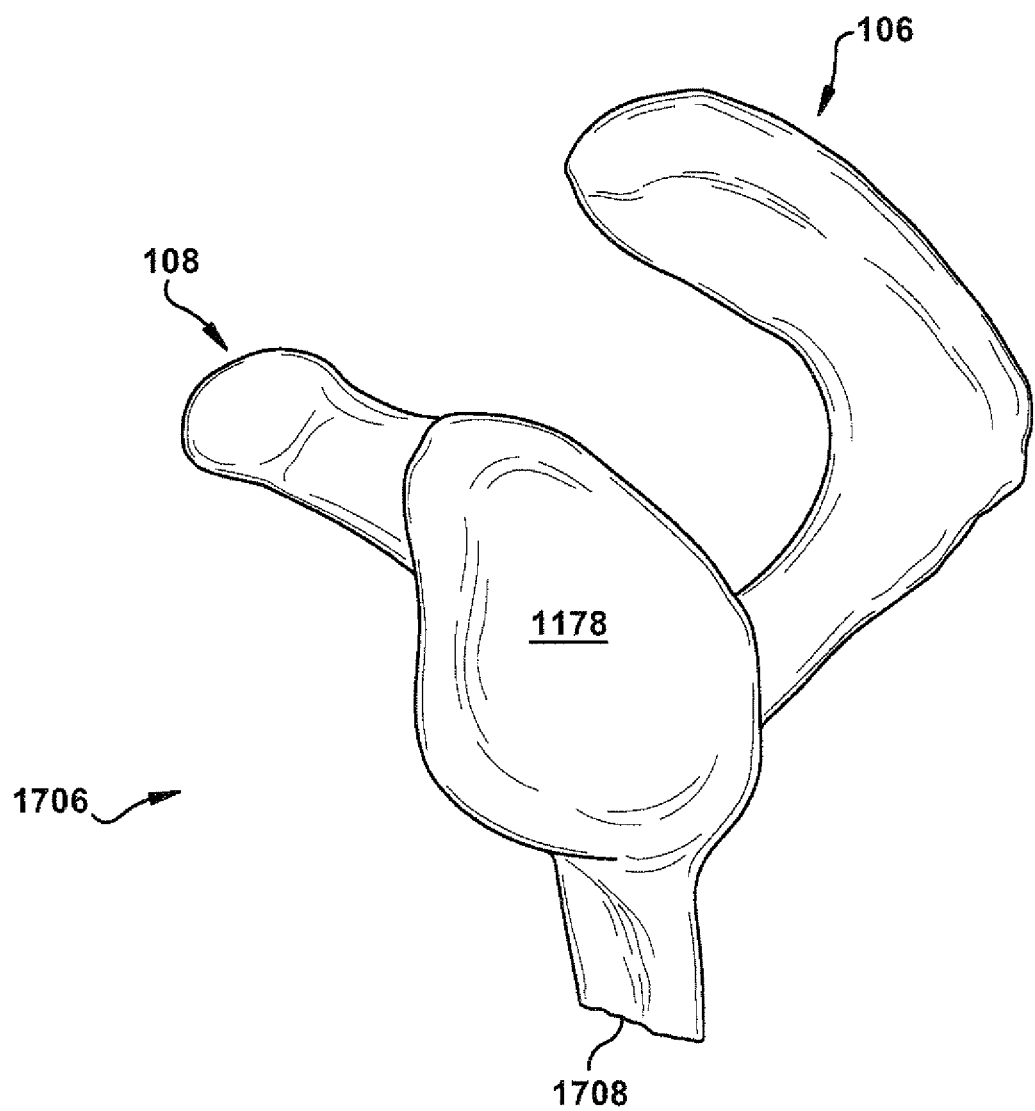
FIGS. 17A-17C are perspective views of a physical native tissue model in a first configuration.
Figure 17B:
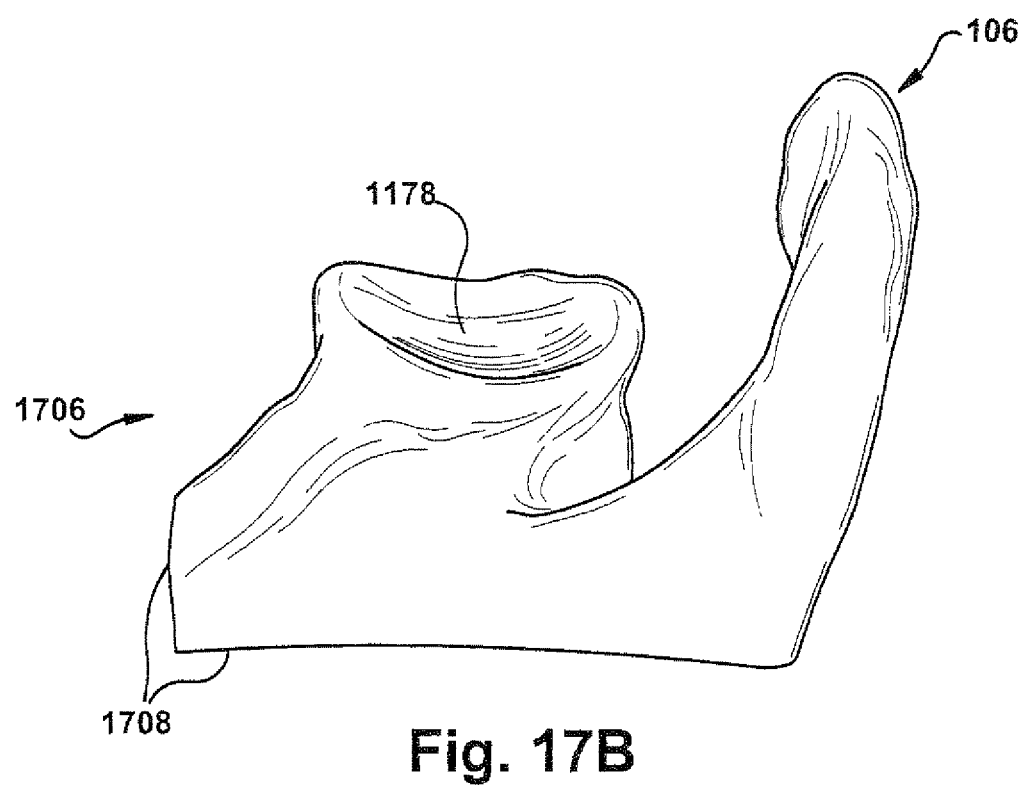
Figure 17C:
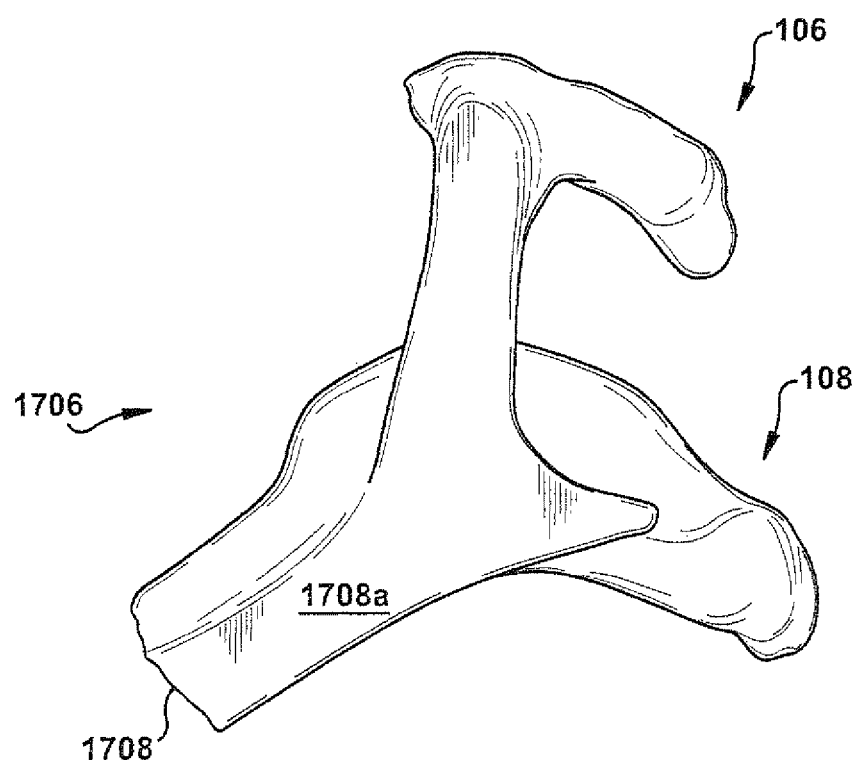

FIGS. 17A-17C depict a physical native tissue model 1706 as a tangible representation of a portion of the virtual model of the native patient tissue shown in FIGS. 16A-16B. (For reasons such as savings of material and manufacturing time, the physical native tissue model 1706 may be fabricated as a portion of a complete virtual model, rather than the entirety of the virtual model.) The physical native tissue model 1706 may be manufactured in any suitable manner such as, for example, using a method (and optionally including additional information) described above as suitable methods for creating the aforementioned tangible representations. When available, a physical native tissue model 1706 may be useful in many different contexts, such as preoperative planning, patient education, visualization, practice, and implementation of the surgical procedure by the user (e.g., for assisting with performing the surgery using patient specific templates and/or adjustable surgical instruments). To that end, the physical native tissue model 1706 may include at least one information feature providing clinically useful information to the user. "Clinically useful" information is used herein to indicate any information, other than the structure of the native patient tissue itself, that assists one of ordinary skill in the art with, for example, some pre- and/or intraoperative task. An "information feature" is any physical feature or characteristic of the physical native tissue model 1706 which signifies or communicates the clinically useful information to the user, optionally in combination with a preoperative plan. Optionally, the information feature may be substantially separated from the surface of interest.

For example, and as shown in FIGS. 17A-17C, a portion of the scapula 100 may be fabricated as a physical native tissue model 1706, with planar faces 1708 bounding the omitted portions of the scapula 100. Those planar faces 1708 may be chosen at predetermined distances from, and/or with predetermined orientations with respect to, a surface of interest (here, the glenoid fossa 1178) on the physical native tissue model 1706. In other words, the physical native tissue model 1706 includes at least one primary patient tissue area including a surface of interest. In the embodiment shown in FIGS. 17A-17C, the primary patient tissue area is the glenoid fossa 1178 because at least a portion of the glenoid fossa surface will be machined or otherwise subjected to substantially permanent physical alteration (e.g., the implantation of a glenoid component 216) during the surgical procedure.

The physical native tissue model 1706 also includes at least one secondary patient tissue area including no surfaces of interest. In the embodiment shown in FIGS. 17A-17C, the majority of the physical native tissue model 1706 is a secondary patient tissue area, because patient tissue surrounding the glenoid fossa 1178 (e.g., the acromion and coracoid processes 106 and 108) does not include any surfaces of interest for the described surgical procedure.

The physical native tissue model 1706 also includes a base surface for engaging a supporting structure. Here, the base surface is planar face 1708a, which simply sits upon a table or other supporting structure (not shown) to present the glenoid fossa 1178 to the user for easy viewing, but any other base surface and corresponding supporting structure (e.g., an interlocking, magnetic, adhesive, or other arrangement) could be provided by one of ordinary skill in the art.

The physical native tissue model 1706 includes in it, as generated, at least one information feature providing clinically useful information to the user. The term "as generated" is used herein to mean "as brought into existence" or "as originated by a vital, chemical, or physical process". In other words, the physical native tissue model 1706 is not made, and then provided to the user for inclusion of the information feature. Instead, during the process of making the physical native tissue model 1706, the information feature is integrally formed with the structure of the physical native tissue model and/or is generated by the manufacturing agent as part of the service of making the physical native tissue model. For example, the virtual model of the patient tissue could be manipulated in the computer system 1582 (optionally, under the direction of the user) to include the information feature in an instruction file that is provided to a rapid prototyping machine for manufacturing the physical native tissue model 1706. Regardless of the way that the information feature is associated with the physical native tissue model 1706, it is contemplated that the information feature will be included when the user initially receives the physical native tissue model and the user does not place the information feature on/in the physical native tissue model.

In many applications of the present invention, the information feature will be substantially separated from the surface of interest on the physical native tissue model 1706. For example, the information feature may be a predetermined orientation of the base surface which is operative to position at least one surface of interest in a predetermined orientation in space when the base surface is engaged with the supporting structure—this concept will be discussed further below with reference to FIGS. 26A-26D. In the embodiment shown in FIGS. 17A-17C, a planar face 1708a bounding a lower portion of the physical native tissue model 1706 may be oriented to be substantially parallel to a sagittal plane of the patient's body. Often the patient is oriented during surgery (with the surface of interest minimally exposed) such that the plane of the scapula 100 is not readily discernable with reference to the orientation of the glenoid vault 110 or glenoid fossa 1178 surface in the surgical field, although it is possible for patients to be oriented during surgery with their scapular plane substantially in a predetermined orientation in space. Accordingly, by placing the physical native tissue model 1706 with an information feature in a known position (e.g, by placing an appropriately configured planar face 1708a of the physical native tissue model flat on a table or other supporting structure), one of ordinary skill in the art can position the glenoid fossa 1178 of the physical native tissue model in a similar orientation to the glenoid fossa of a pre-positioned patient or can, alternatively, orient the patient such that the patient's glenoid fossa 1178 substantially matches the orientation of that of the physical native tissue model placed upon a supporting surface for intraoperative reference purposes.

Through use of a physical native tissue model 1706 which is positioned in space (optionally with the aid of an information feature such as the preconfigured planar face 1708a) analogously to the actual patient tissue in the operating room, a user can readily envision obscured portions of the patient's native tissue anatomy through reference to the physical native tissue model 1706. The physical native tissue model 1706 may be configured to provide the user with a visualization of the native patient tissue in the same orientation as in the patient's body but without the surrounding tissue that prevents the user from directly seeing structures such as, but not limited to, the acromion process 106, the coracoid process 108, or any other structure of the scapula 100. This may be particularly useful when the physical native tissue model 1706 is fabricated at a 1:1 scale with the native patient anatomy, but also will have utility when the model is scaled up or down from the patient's actual tissue.

Optionally, the predetermined orientation of the base surface (the planar face 1708*a* in FIGS. 17A-17C) may be chosen to dictate a clinically useful placement of a landmark 538, such as a guide pin, into engagement with the physical native tissue model 1706 when the landmark is located orthogonally to the supporting structure. It may be relatively simple to orient a landmark orthogonal to a table or other supporting structure, perhaps with the aid of a leveling aid (e.g., a bubble level) or setting stand (such as that disclosed in co-pending U.S. Provisional Patent Application No. 61/534,142, filed 13 Sep. 2011 and titled "Apparatus and Method for Transferring Predetermined Spatial Positioning Information to an Adjustable Tool", the entire contents of which are incorporated herein by reference), whereas achieving a particular three-dimensional, non-orthogonal, trajectory of a landmark relative to a surface of interest may be relatively difficult to do accurately without a guiding aid.

For example, if the clinically useful placement of a guide pin is at a predetermined trajectory with respect to the surface of interest, the planar face 1708*a* could be configured at an angle to the surface of interest such that orthogonal placement of the guide pin (or other landmark 538) relative to the surface of interest will achieve the desired predetermined trajectory of the guide pin with respect to the surface of interest. Accordingly, the guide pin could be placed with the assistance of the orthogonally-configured planar face 1708*a*, and then the physical native tissue model 1706 could be manipulated as desired to reposition the surface of interest (with the emplaced guide pin) into a similar orientation to the native patient tissue exposed in the surgical procedure. In such manner, the relatively easily orthogonally-positioned guide pin or other landmark 538 and associated physical native tissue model 1706 could be manipulated into a more clinically useful orientation with respect to the exposed native patient tissue while maintaining the predetermined trajectory of the guide pin. To aid in this effort, the physical native tissue model 1706 could optionally include a planar face 1708*a* including one type of clinically useful information (e.g., the scapular plane information previously referenced), and a separate, optionally attachable/detachable positioning wedge (not shown) having another type of clinically useful information (e.g., information related to the orthogonal-positioning trajectory for the guide pin) could be provided as an intermediate structure between the planar face 1708*a* or other base surface and the supporting structure to facilitate multi-faceted use of the physical native tissue model 1706 for a variety of different interoperative assistance and visualization tasks.

As another example embodiment of a physical native tissue model 1706 giving spatial information, a pin-receiving aperture may be provided in the physical native tissue model, to receive a guide pin and thus demonstrate a certain direction or axis to the user with respect to the native tissue. As a corollary to this example, an axis-, direction-, or plane-indicating structure may extend from the physical native tissue model to serve as a user visualization aid or reference.

Some other examples of clinically useful information that can be embodied in, and/or represented by, a physical native tissue model 1706 include the location of an original joint line location of a deformed patient tissue (to help the user define reconstruction goals), an inference of the location and/or type of deep tissue structures via an included trajectory and/or location of a guide pin, the location of added materials such as tissue (e.g., bone) grafts, the method of fixation, and the trajectory of fixation devices to be added to patient tissue. Another example of clinically useful information can include the location of a "hidden" structure or pathology below the surface of the patient tissue, which may assist the user with finding that structure in three-dimensional space in the patient tissue—this could be facilitated by depicting the "hidden" structure as being noticeably distinct from neighbouring portions of the physical native tissue model 1706. For example, the "hidden" structure could have a particular color, visible through translucent neighbouring/concealing structures and/or visible upon removal of a "breakaway" or otherwise removable portion of a neighbouring structure.

Figure 18A:
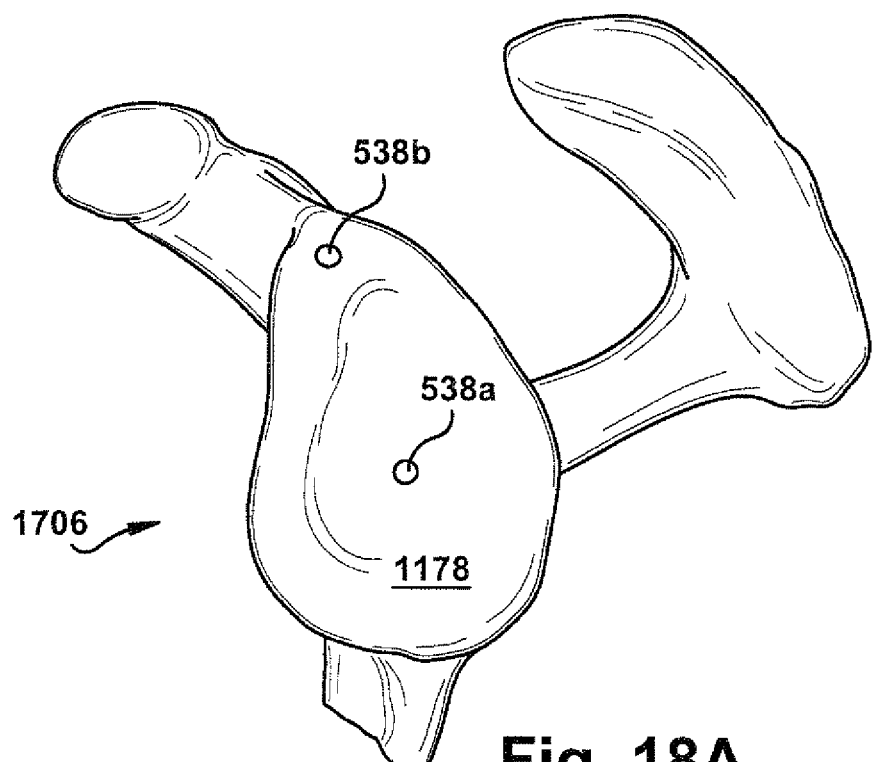
FIGS. 18A-18C are perspective views of the model of FIGS. 17A-17B in a second configuration.
Figure 18B:
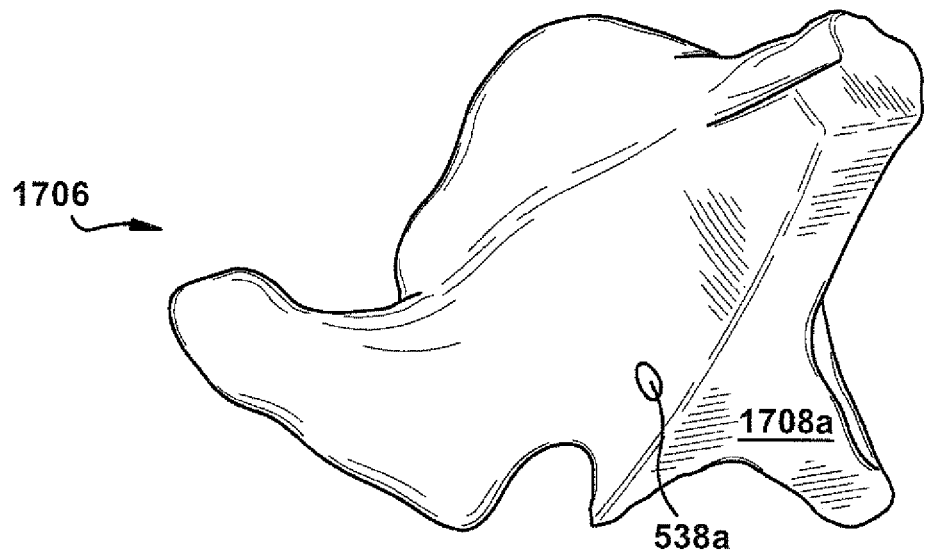
Figure 18C:
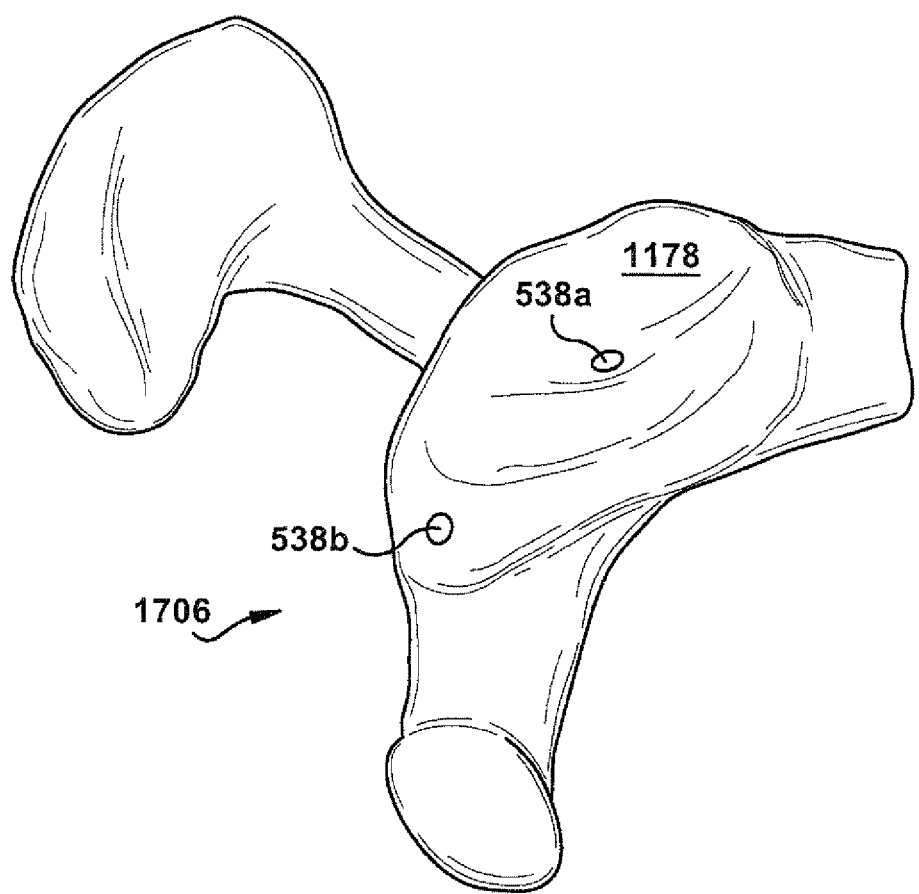

Turning to FIGS. 18A-18C, which illustrate a spatial type of information feature, the physical native tissue model 1706 is shown as having an information feature indicating a desired placement for a landmark 538 (two shown). The landmark(s) 538 information feature(s) indicates at least one of a marking location and a marking trajectory to which reference is made during surgical modification of the patient tissue. For example, the landmark 538 could be a two-dimensional marking on the surface of the physical native tissue model 1706, or could be an aperture, protrusion, or other three-dimensional structure embodying the desired clinically useful information. As shown in FIG. 18A, a first landmark 538*a* is located in the primary patient tissue area (i.e., an area including at least one surface of interest, here the glenoid fossa 1178) and a second landmark 538*b* is spaced apart from the surface of interest and located in the secondary patient tissue area (i.e., an area which includes no surfaces of interest). In other words, the second landmark 538*b* is spaced apart from the surgical modification location at which the glenoid component 216 will be placed in the surgical procedure for which the depicted physical native tissue models 1706 are being prepared, as will become apparent with reference to succeeding Figures.

As can be seen in FIGS. 18A-18B, the second landmark 538*b* may be an aperture extending through the body of the physical native tissue model 1706. Optionally, this aperture may be sized to accept a guide pin (not shown), such that the guide pin itself extends from the physical native tissue model 1706 and acts as the landmark 538*b*, to demonstrate both the marking location and the marking trajectory at a glance to the user, in a readily discernible format. Whether or not a guide pin or other readily discerned aid is used, the clinically useful information embodied in the information feature (whether a landmark 538 or some other type) may be transferred from the physical native tissue model 1706 to the native patient tissue during a surgical procedure, in any suitable manner.

The exact mechanism of transfer of the clinically useful information may vary greatly depending upon such factors as the nature of the clinically useful information, the nature of the information feature, the structure of the physical native tissue model 1706, the structure of the patient's actual native tissue, the surgical procedure being performed, the nature of any assisting devices, the preferences of the user, or the like. In its simplest form, this clinically useful information could be transferred mainly by the user's "eye-balling" or estimating the location of a landmark 538 or some other clinically useful information and trying to duplicate the landmark 538 location on the patient's tissue.

One example of a more sophisticated method of the transfer of clinically useful information between a physical native tissue model 1706 and a native patient tissue during a surgical procedure includes adjusting a reusable surgical instrument to transfer at least a portion of the clinically useful information embodied in the information feature. Suitable reusable surgical instruments include, but are not limited to, calipers, protractors, other manually operated measuring tools, custom-made or stock adjustable mechanical frames (e.g., pantographs), electronic location aids (e.g., stereotactic surgical systems or other aided navigation systems), patient-specific templates or aids such as those disclosed in co-pending U.S. Provisional Patent Application Nos. 61/536,756, filed Sep. 20, 2011 and titled "Method and System for Producing at least one Patient-Specific Surgical Aid" and 61/408,359, filed 29 Oct. 2010 and titled "System and Method for Association of a Guiding Aid with a Patient Tissue" (the entire contents of both of which are incorporated herein by reference), the tool disclosed in co-pending U.S. patent application Ser. No. 12/854,362, filed 11 Aug. 2010 and titled "Method and Apparatus for Insertion of an Elongate Pin Into a Surface" (the entire contents of which are incorporated herein by reference), and the tools disclosed in co-pending U.S. Provisional Patent Application No. 61/534,152, filed 13 Sep. 2011 and titled "Method and Apparatus for Insertion of an Elongate Pin into a Surface" (the entire contents of which are incorporated herein by reference).

As another option for transferring clinically useful information between a physical native tissue model 1706 and a native patient tissue during a surgical procedure, at least one patient-specific surgical aid (not shown) could be generated via interaction with the physical native tissue model and with the information feature. For example, a system such as, but not limited to, that disclosed in the aforementioned co-pending U.S. Provisional Patent Application No. 61/536,756, filed Sep. 20, 2011 and titled "Method and System for Producing At Least One Patient-Specific Surgical Aid" (previously incorporated by reference) could be used to replicate at least a portion of the surface of the physical native tissue model 1706 with the landmark(s) 538 somehow memorialized therein. The user can then transfer the clinically useful information by aligning some feature of the patient-specific surgical aid with the patient's native tissue in a way that substantially "registers" the patient-specific surgical aid on the native tissue in the same orientation as the patient-specific surgical aid was oriented on the physical native tissue model 1706. The placement of the landmark(s) 538 or other clinically useful information will then be readily transferred to, and/or used with, the native tissue with a high degree of user confidence in the replication.

The physical native tissue model 1706 could be used to interact with an implant or instrument before or during the surgical procedure, as well. For example, a user could rehearse certain interactions of an implant or instrument with the physical native tissue model 1706 to gain familiarity with the way that the implant or instrument is likely to intraoperatively interact with the patient's native tissue.

Figure 19A:
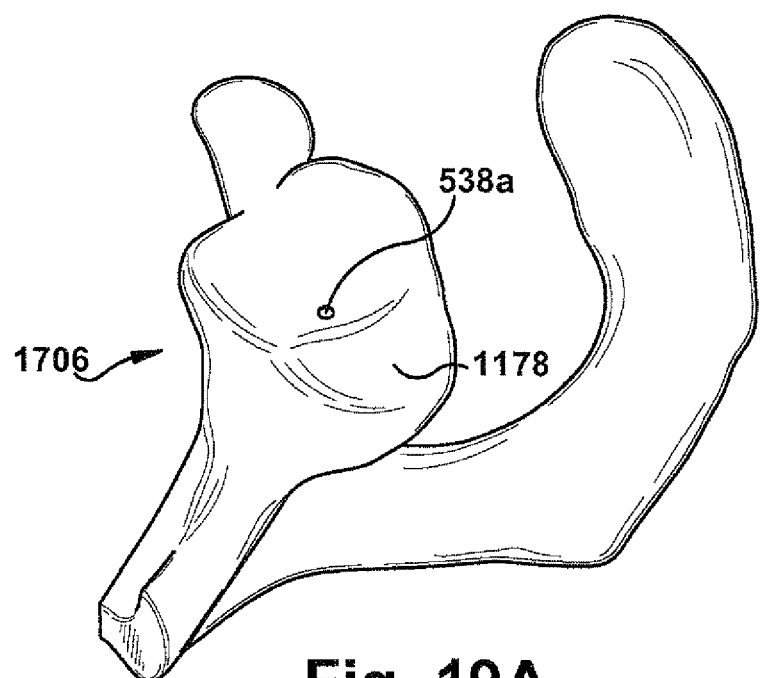
FIGS. 19A-19B are perspective views of the model of FIGS. 17A-17B in a third configuration.
Figure 19B:
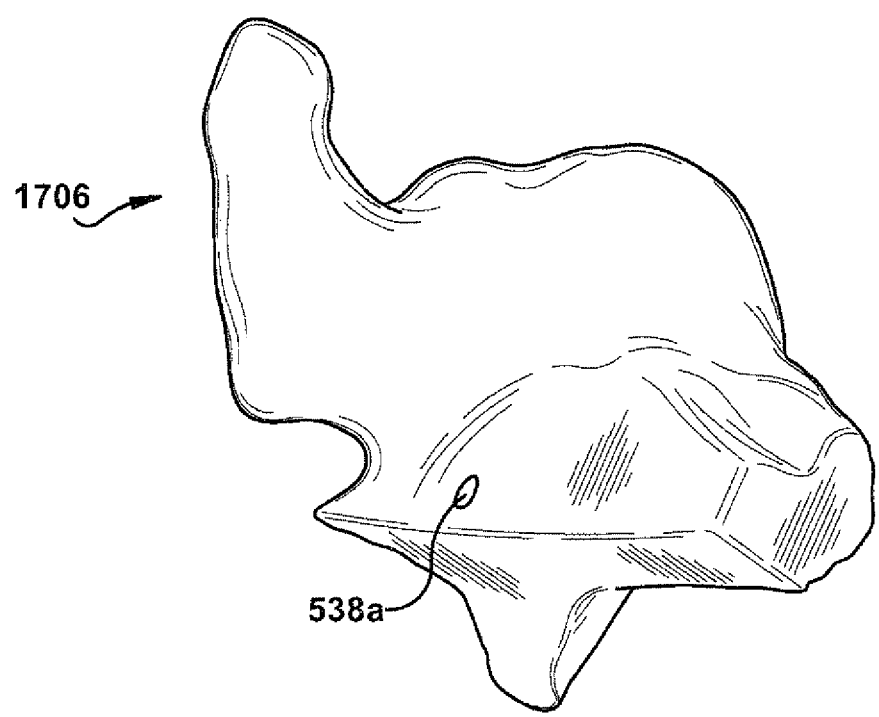

FIGS. 19A-19B depict a physical native tissue model 1706 which has undergone some initial tissue preparation (here, a portion of the glenoid fossa 1178, toward the upper left in the orientation of FIG. 19A, has been reamed away). Through use of a physical native tissue model 1706 similar to that shown in FIGS. 19A-19B, a user can visualize an intermediate or initial step in machining the patient tissue.

FIGS. 20A-22B depict different views of a series of physical native tissue models 1706 which include, as generated, information features which include, in addition to landmark 538b, clinically useful information relating to the machining of the surface of interest to accept a prosthetic implant (here, glenoid component 216) to be installed in the native patient tissue. In the physical native tissue model 1706 of FIGS. 20A-20B, an initial reaming process has been performed (a more extensive process than the reaming shown in FIGS. 19A-19B) and the initial glenoid fossa 1178 has been machined away to reveal the material of the glenoid vault 110. Here, the reaming has been accomplished to accommodate a variable-depth glenoid component 216 of a known variety. Landmark 538a remains and, since it is an aperture extending into the body of the physical native tissue model 1706, it will continue to be apparent as the machining away of the material progresses.

Figure 20A:
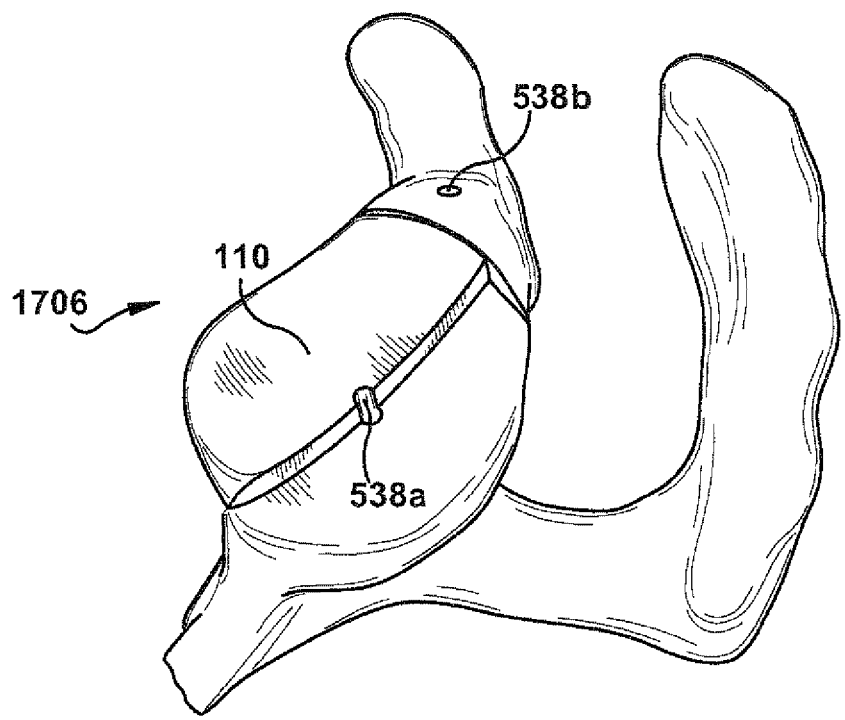
FIGS. 20A-20B are perspective views of the model of FIGS. 17A-17B in a fourth configuration.
Figure 20B:
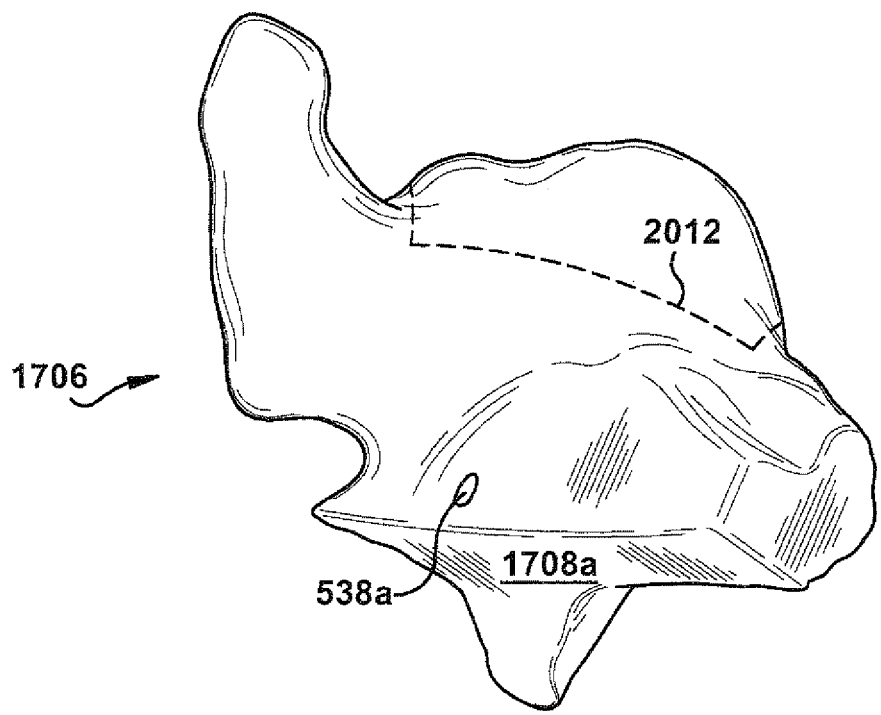
Figure 21A:
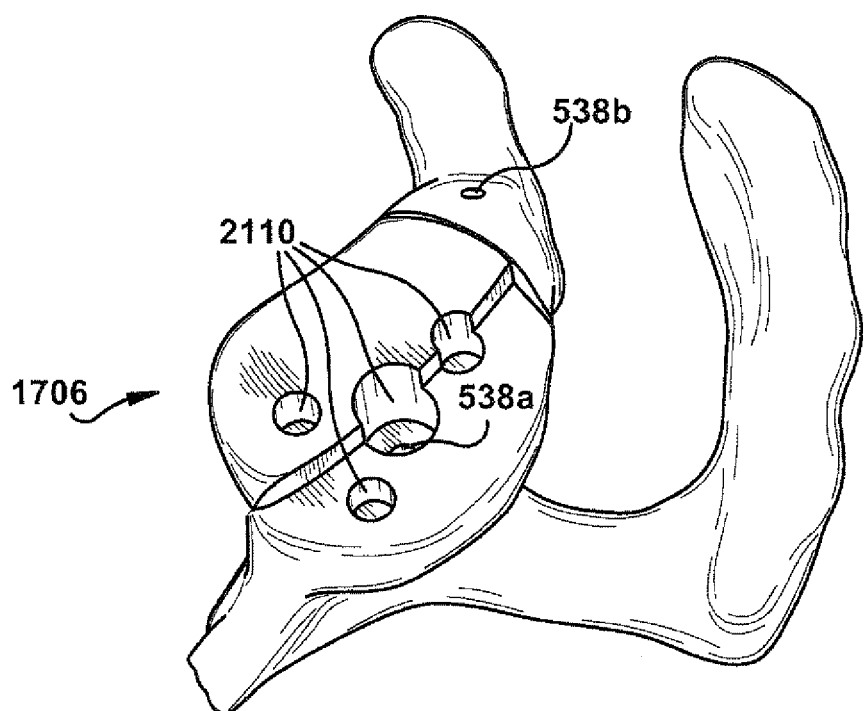
FIGS. 21A-21B are perspective views of the model of FIGS. 17A-17B in a fifth configuration.
Figure 21B:
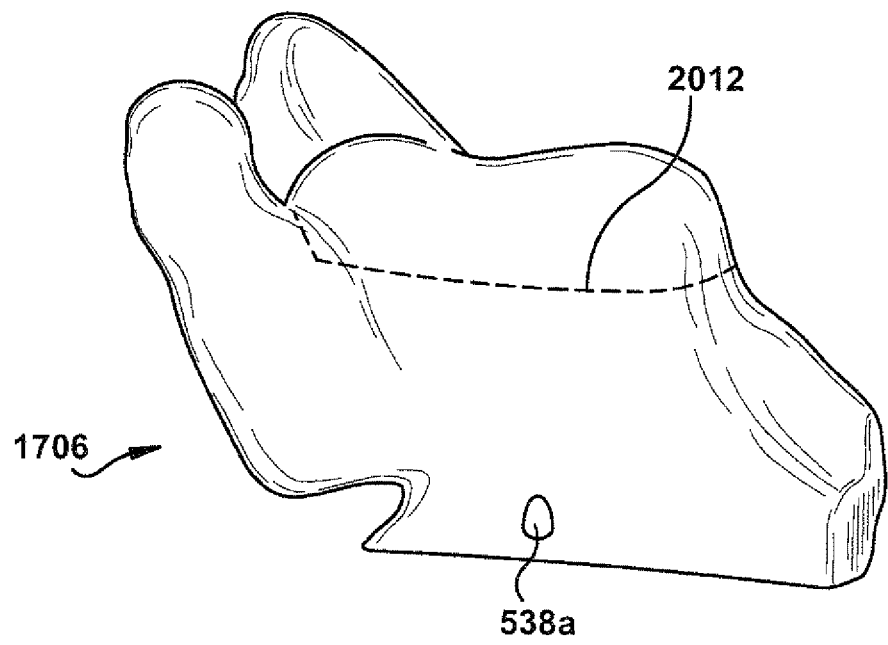

Proceeding to FIGS. 21A-21B, the physical native tissue model 1706 is another version which includes, as generated, information features relating both to the reaming process shown in the FIGS. 20A-20B implant and to the drilling (location, trajectory, and depth) of a plurality of apertures which may be helpful in accommodating, for example, a device shaft 540 of a known type of stock or custom prosthetic glenoid component 216.

Figure 22A:
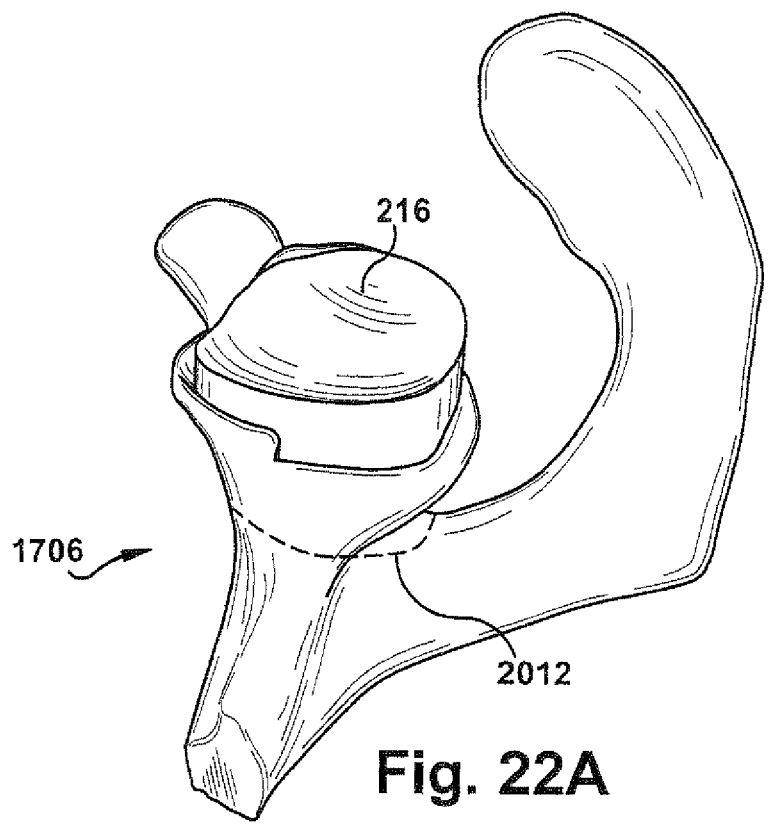
FIGS. 22A-22B are perspective views of the model of FIGS. 17A-17B in a sixth configuration.
Figure 22B:
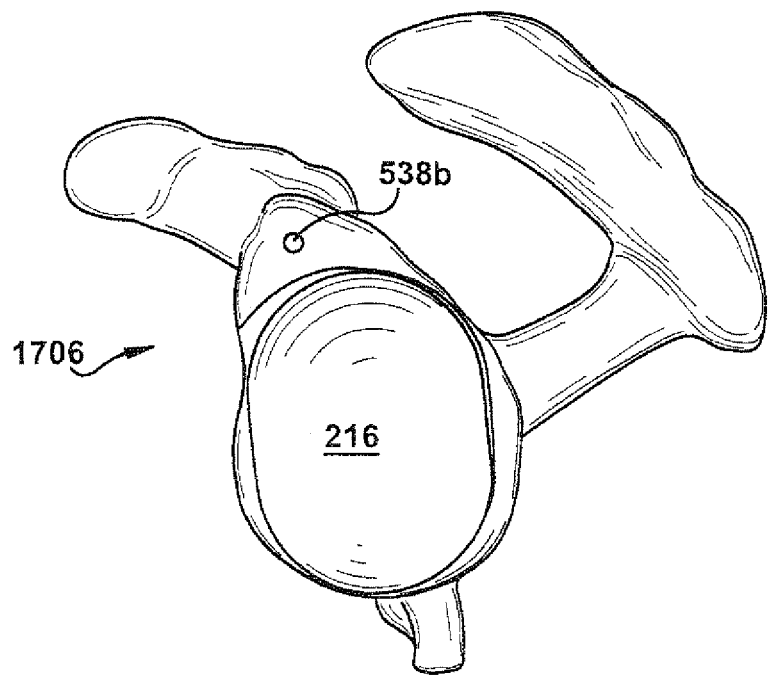

The next physical native tissue model 1706 provided is shown in FIGS. 22A-22B and includes, as generated, an information feature structure replicating at least a portion of the prosthetic implant (here, glenoid component 216) in a preoperatively planned installed position.

By using the sequence of different physical native tissue models 1706 shown successively in FIGS. 19A-19B, 20A-20B, 21A-21B, and 22A-22B, the user can be provided with visual and tactile depictions of clinically useful information regarding each major step in the surgical procedure. Reference can be made to each of these physical native tissue models 1706 at an appropriate time during the surgery to remind the user of the preoperative plan, to provide measurements for transference of the clinically useful information to the patient's native tissue, to verify the mechanical operations being done to the patient's native tissue, or for any other reason. A user could hand-make a series of physical native tissue models 1706 having the "stepwise" surgical phases shown in the physical native tissue models of FIGS. 19A-19B, 20A-20B, 21A-21B, and 22A-22B during preoperative planning, and even refer to these handmade models during the surgical procedure. However, it should be understood that the present invention contemplates that each of the sequence of physical native tissue models 1706 shown successively in FIGS. 19A-19B, 20A-20B, 21A-21B, and 22A-22B is generated with the clinically useful "stepwise" information already contained therein, such that the physical native tissue models each accurately replicate the dimensions, placement, orientation, and other properties of the preoperatively determined surgical plan for a major step of the surgery. Similarly, while a user could create, from "blank" models of a patient's tissue, physical native tissue models 1706 having simple cutting plane or drilling location markings, the physical native tissue models 1706 shown successively in FIGS. 19A-19B, 20A-20B, 21A-21B, and 22A-22B each include information features giving a wealth of clinically useful information about the substantially permanent physical modifications to be made during the surgical procedure that would not be available if the user were simply given a "resection line here" or other simple two-dimensional landmark. For example, the depth, dimensions, and trajectory of the preoperatively planned apertures 2110 in FIG. 21A would be extremely difficult to communicate to a user through simple markings, but are readily available to the user of the physical patient tissue model 1706 shown in FIGS. 21A-21B without requiring that user to reference a virtual patient tissue model during the surgery.

Optionally, and as shown schematically in the Figures, the sequence of physical native tissue models 1706 shown successively in FIGS. 19A-19B, 20A-20B, 21A-21B, and 22A-22B may each be made in a modular fashion to economize on space, fabrication costs, sterilization requirements, or for any other reason. More specifically a module line 2012 is shown on several of the depicted physical native tissue models 1706 as delineating a lower portion of the physical native tissue model as a "holder base", as referenced herein. The holder base does not physically change across the sequence of physical native tissue models 1706 shown successively in FIGS. 19A-19B, 20A-20B, 21A-21B, and 22A-22B. Accordingly, the upper portion (above the module line 2012) of the physical native tissue model 2012, which includes the surface of interest (here, the glenoid fossa 1178 and the machined features which supplant the original glenoid fossa surface) can be a separate piece which is selectively mated with the holder base for reference by the user. When the physical native tissue models 1706 are made in this modular fashion, the bulk of the physical native tissue model (the unchanged holder base portion, approximately below the module line 2012) can remain the same and have a series of partial native patient tissue models, each depicting the surface of interest at a different step in the surgical procedure, successively exchanged for one another as the surgical procedure progresses. As long as each partial native patient tissue model (including the surface of interest) mates appropriately with the holder base, the manufacture of the series of physical native tissue models 1706 shown successively in FIGS. 19A-19B, 20A-20B, 21A-21B, and 22A-22B can then be simplified while still including all of the information shown in these Figures.

FIGS. 23A-25B depict a physical native tissue model 1706' according to a second embodiment of the present invention. The physical native tissue model 1706' of FIGS. 23A-25B is similar to the physical native tissue model 1706 of FIGS. 17A-22B and therefore, structures of FIGS. 23A-25B that are the same as or similar to those described with reference to FIGS. 17A-22B have the same reference numbers with the addition of a "prime" mark. Description of common elements and operation similar to those in the previously described first embodiment will not be repeated with respect to the second embodiment.

Figure 23A:
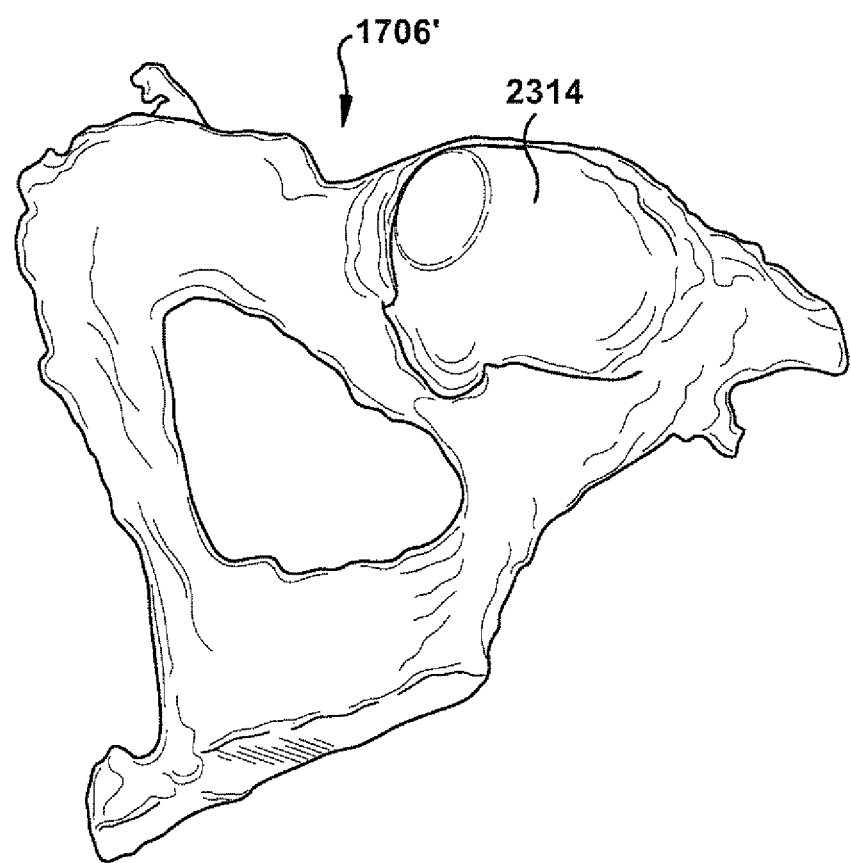
FIGS. 23A-23B are perspective views of a physical native tissue model in a first configuration.
Figure 23B:

The physical native tissue models 1706' shown successively in FIGS. 23A-23B, 24A-24B, and 25A-25B depict a portion of a pelvis and can be used in conjunction with a hip replacement surgery in much the same way that the partial scapula physical native tissue models 1706 shown in FIGS. 20A-20B, 21A-21B, and 22A-22B can be used in conjunction with a shoulder replacement surgery. FIGS. 23A-23B depict an acetabulum 2314 of interest, including at least one landmark 538' (shown in the bottom perspective view of FIG. 23B but optionally extending as an aperture through a thickness of the physical native patient tissue model 1706' to provide a landmark function to the acetabulum).

Figure 24A:
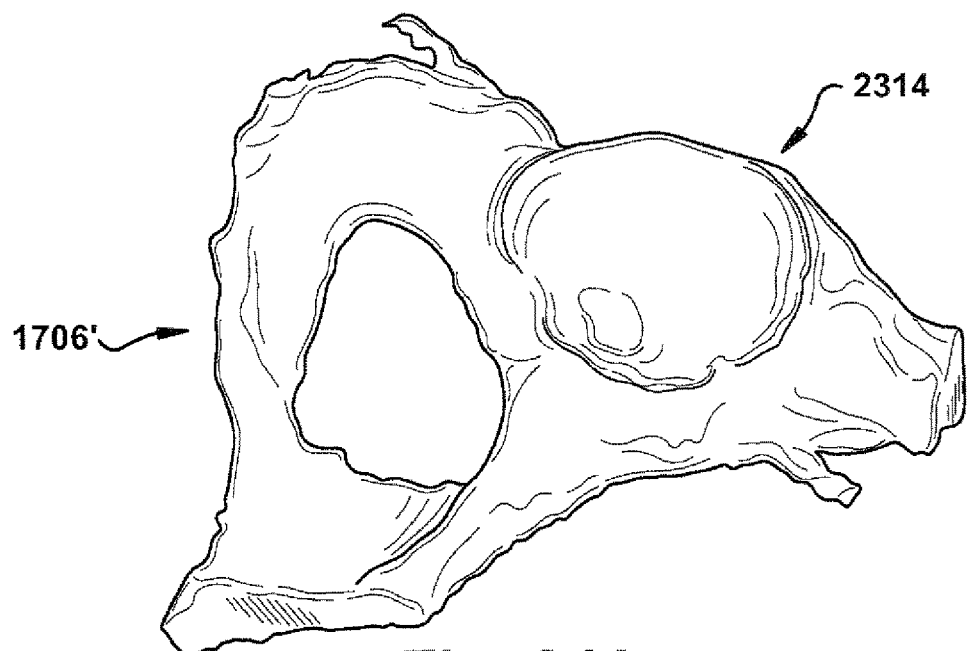
FIGS. 24A-24B are perspective views of the model of FIGS. 23A-23B in a second configuration.
Figure 24B:
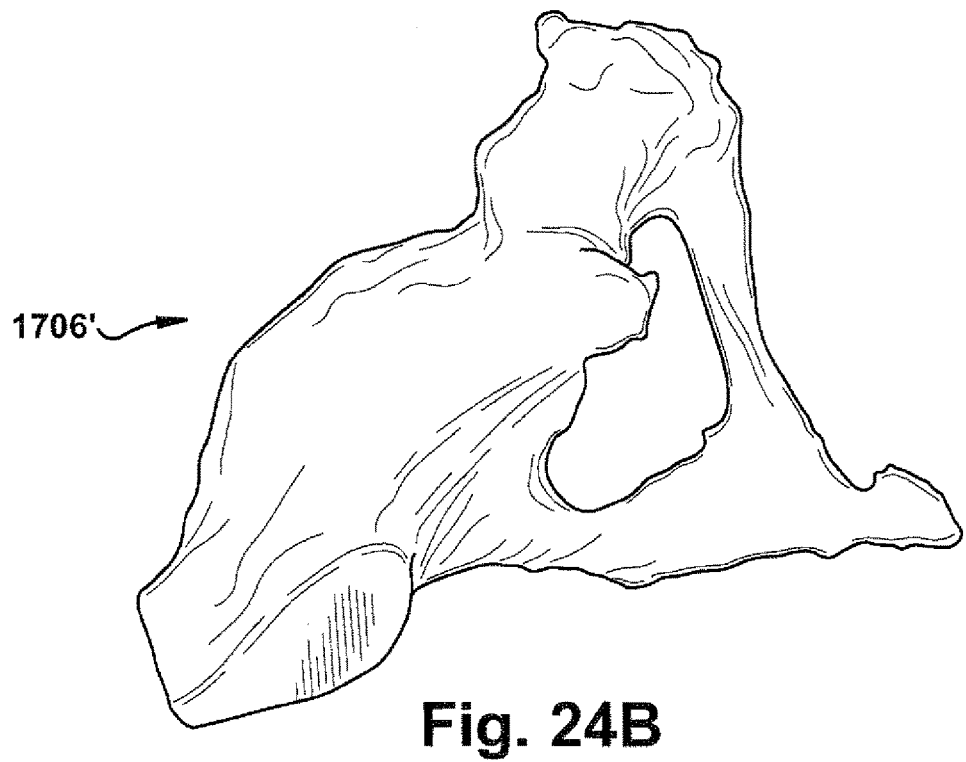
Figure 25A:
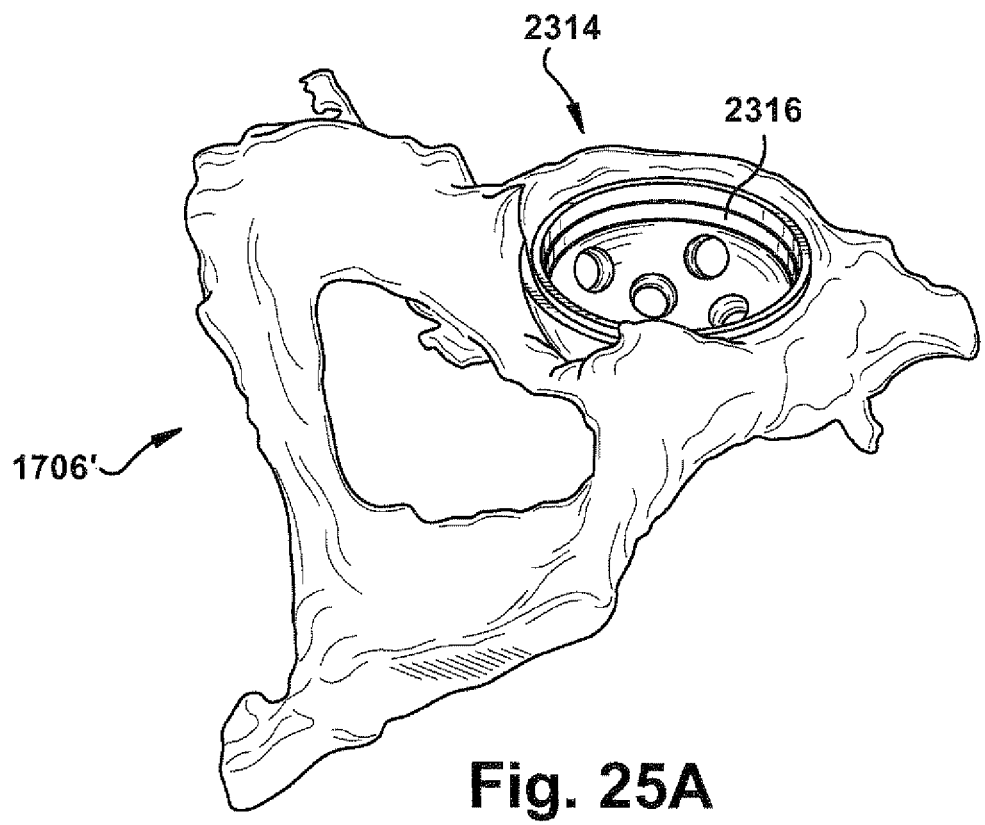
FIGS. 25A-25B are perspective views of the model of FIGS. 23A-23B in a third configuration.
Figure 25B:
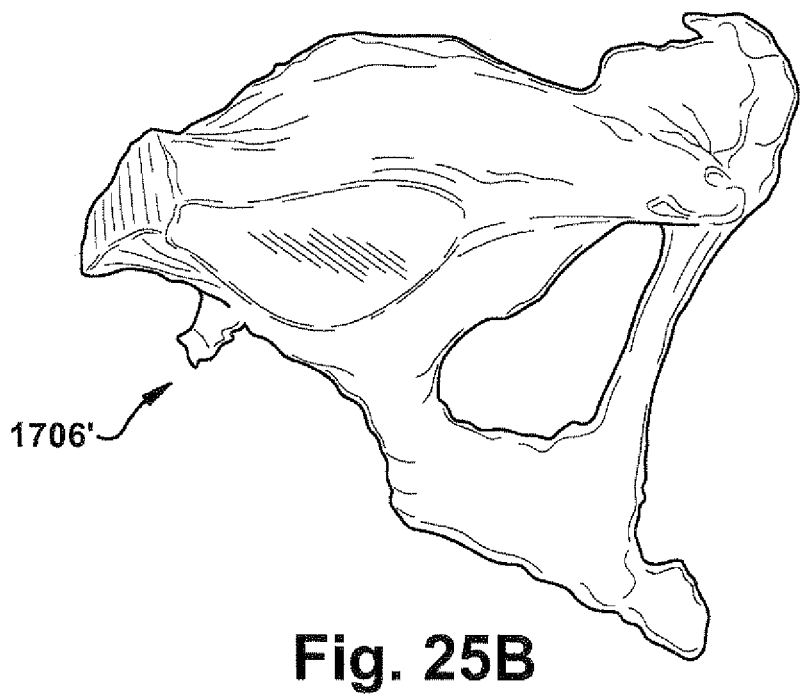

In the version of the physical native patient tissue model 1706' shown in FIGS. 24A-24B, the acetabulum 2314 is depicted, as generated, as having undergone initial reaming. In the version of the physical native patient tissue model 1706' shown in FIGS. 25A-25B, an acetabular component 2316 of a prosthetic hip replacement device is depicted, as generated, in the desired preoperatively determined position with respect to the acetabulum 2314.

FIGS. 26A-26D depict a physical native tissue model 1706" according to a third embodiment of the present invention. The physical native tissue model 1706" of FIGS. 26A-26D is similar to the physical native tissue model 1706 of FIGS. 17A-22B and therefore, structures of FIGS. 26A-26D that are the same as or similar to those described with reference to FIGS. 17A-22B have the same reference numbers with the addition of a double "prime" mark. Description of common elements and operation similar to those in the previously described first embodiment will not be repeated with respect to the third embodiment.

The physical native tissue model 1706" of FIGS. 26A-26D includes an information feature which is shown as a patient-specific base 2618 embodying multiple types of clinically useful information, as alluded to above with reference to planar face 1708a. That is, the patient-specific base 2618 of the third embodiment of the physical native tissue model 1706" is configured to convey clinically useful information to the user by virtue of interaction between the patient-specific base 2618 (or portions thereof) and an underlying support surface on which the physical native tissue model 1706" is resting.

Figure 26A:
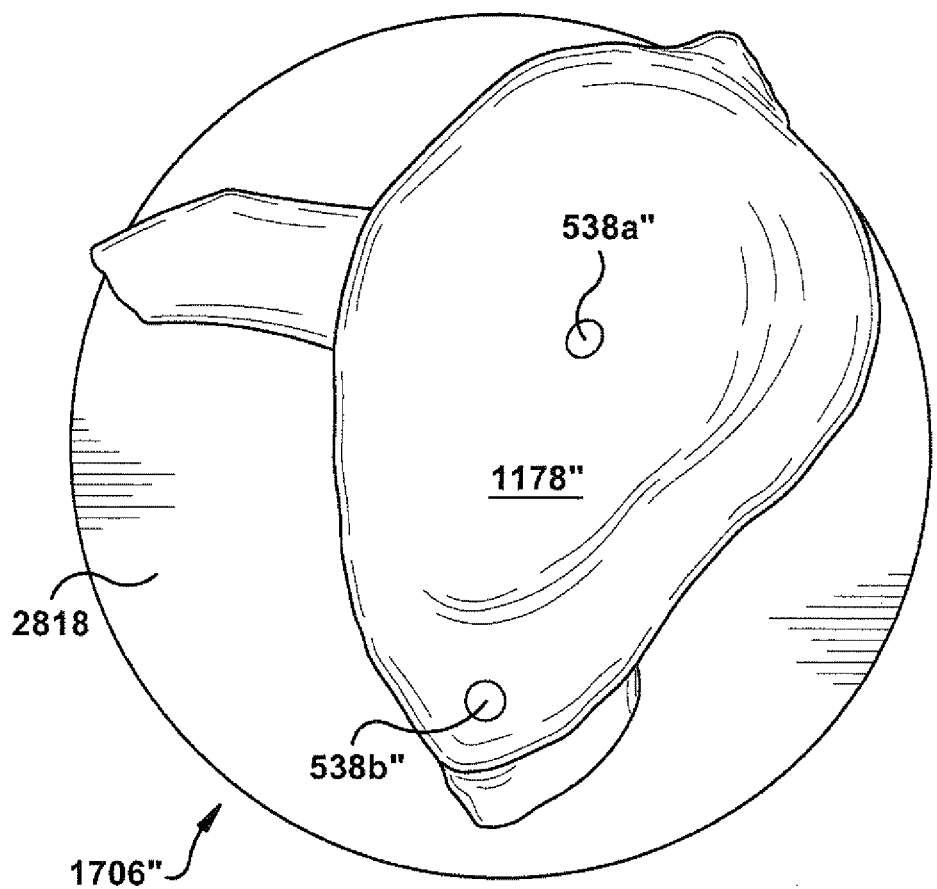
Figure 26C:
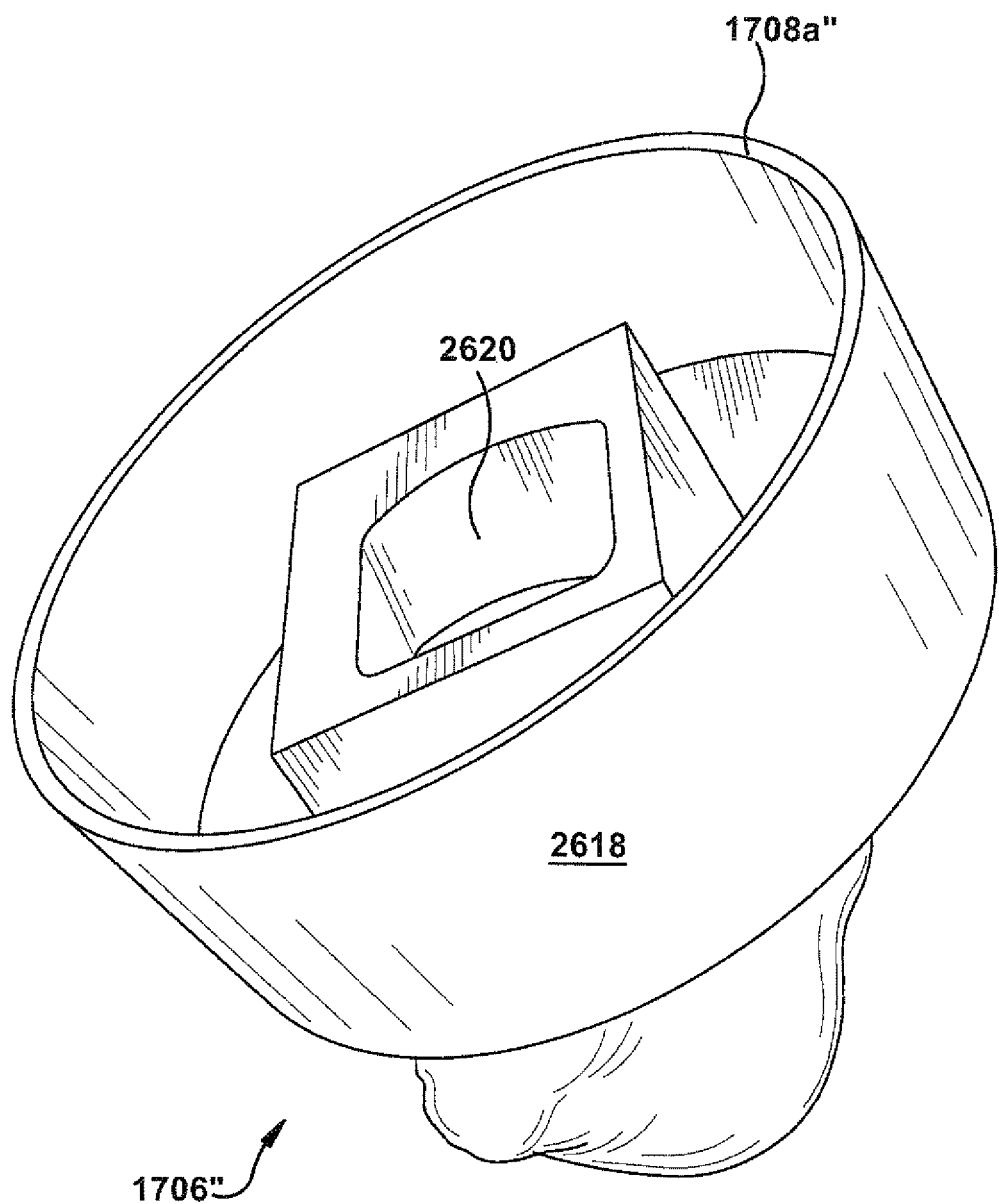
Figure 26D:
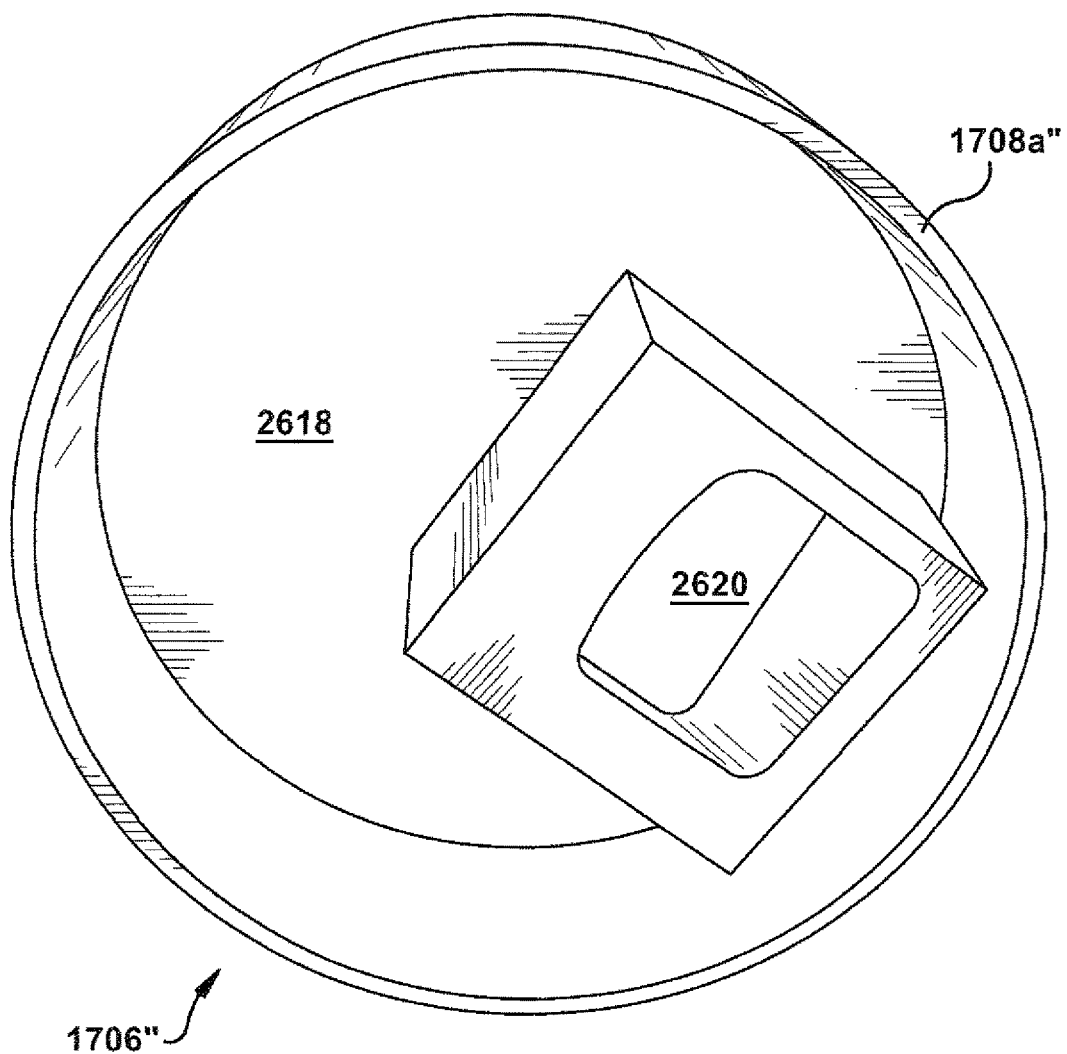

For example, the planar face 1708a" shown in FIGS. 26B-26D is a lower rim of the substantially cylindrical patient-specific base 2618. When the physical native tissue model 1706" is resting atop a substantially planar (and parallel to the ground) first supporting surface (not shown), the planar face 1708a" holds the depicted patient tissue with the glenoid fossa 1178" surface substantially perpendicular to the plane of the scapula. However, the patient-specific base 2618 includes an auxiliary orienting feature 2620 which is configured (e.g., via shape, size, orientation, or any other physical characteristic) to rest atop a suitable second supporting surface and convey different clinically useful information than when the physical native tissue model 1706" is supported by the first supporting surface.

As may be seen in FIGS. 26C and 26D, for example, the auxiliary orienting feature 2620 is shaped to mate with, and be supported by, a second supporting surface which interacts with the auxiliary orienting feature 2620 to hold the physical native tissue model 1706" in a desired orientation in space. An example of a suitable second supporting surface is the D-shaped lug shown in certain embodiments of the previously incorporated co-pending U.S. Provisional Patent Application No. 61/534,142, filed 13 Sep. 2011 and titled "Apparatus and Method for Transferring Predetermined Spatial Positioning Information to an Adjustable Tool". When the auxiliary orienting feature 2620 is dictating a spatial orientation of the rest of the physical native tissue model 1706" shown in FIGS. 26A-26D, a guide pin inserted in at least one landmark 538a" and 538b" will be held substantially perpendicular to an underlying ground surface, without regard to the spatial orientation of the glenoid fossa 1178". The "dual purpose" physical native tissue model 1706" shown in FIGS. 26A-26D therefore has multiple information features embodied therein, each of which may be useful to the user for different reasons and at different times before, during, and/or after the surgical procedure.

The physical native tissue model 1706 from any embodiment of the present invention could be used for patient or professional education before or after the surgical procedure, as well, to explain the surgical procedure to the patient or an advocate; to show an insurer, other third-party payer, follow-up medical professional, or other party the extent and nature of the surgical procedure; in a classroom setting to help train others in the procedure done; as part of a scientific/research study or presentation; or simply as a "souvenir" for the patient or user to memorialize the surgical procedure.

Physical native tissue models 1706 with information features or specific landmarks 538 related to the preoperatively developed surgical plan are not currently provided or used as references during surgical procedures. The availability of a physical native tissue model 1706 to use as a reference in this manner may supplement or even supplant the need for intraoperative imaging, which is likely to reduce cost, operating room clutter, and time required for the surgical procedure.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described system are merely illustrative; one of ordinary skill in the art could readily determine any number of tools, sequences of steps, or other means/options for virtually or actually placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. An adhesive (such as, but not limited to, bone cement) could be used in conjunction with the system and method described herein. The patient-specific template 750 and/or the patient-specific placement guide 958 may include a plurality of structures cooperatively forming the base body and temporarily or permanently attached together in such a manner as to permit relative motion (e.g., pivoting, sliding, or any other motion) therebetween. The patient-specific placement guide 958 may not actually be patient-specific but could instead be a stock item in situations where the landmark(s) 538 are placed to "standardize" a particular native patient tissue model with a standard frame of reference. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. Clinically useful information could include written or other legible information, as well as spatial or other physically discernible information. The system is described herein as being used to plan and/or simulate a surgical procedure of implanting one or more prosthetic structures into a patients body, but also or instead could be used to plan and/or simulate any surgical procedure, regardless of whether a non-native component is left in the patient's body after the procedure. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A method for assisting a user with surgical implementation of a preoperative plan, the method comprising the steps of:
    generating a physical native tissue model of a native patient tissue, the physical native tissue model including at least one primary patient tissue area including a surface of interest, at least one secondary patient tissue area including no surfaces of interest, and a base surface for engaging a supporting structure; and
    including in the physical native tissue model, as generated, at least one information feature providing clinically useful information to the user;
    wherein the surface of interest is a surface upon/into which a prosthetic device is to be placed or a surface which is to be the main subject of substantially permanent physical modification during a surgical procedure in an effort to provide therapeutic benefit to the patient;
    wherein the information feature is any physical feature or characteristic of the physical native tissue model which signifies or communicates the clinically useful information to the user; and
    wherein the information feature is substantially separated from the surface of interest.

2. The method of claim 1, wherein the step of providing a physical native tissue model of a native patient tissue includes the steps of:
    creating a virtual model of a native patient tissue; and
    creating a physical native tissue model of the native patient tissue as a tangible representation of the virtual model of the native patient tissue.

3. The method of claim 1, wherein the information feature is a predetermined orientation of the base surface which is operative to position at least one surface of interest in a predetermined orientation in space when the base surface is engaged with the supporting structure.

4. The method of claim 3, wherein the predetermined orientation of the base surface is chosen to dictate a clinically useful placement of a landmark into engagement with the physical native tissue model when the landmark is located orthogonally to the supporting structure.

5. The method of claim 1, wherein the information feature indicates a desired placement for a landmark, the landmark indicating at least one of a marking location and a marking trajectory to which reference is made during surgical modification of the native patient tissue.

6. The method of claim 1, including the step of transferring the clinically useful information embodied in the information feature from the physical native tissue model to the native patient tissue during a surgical procedure.

7. The method of claim 6, wherein the step of transferring the clinically useful information embodied in the information feature includes the step of adjusting a reusable surgical instrument to transfer at least a portion of the clinically useful information embodied in the information feature from the physical native tissue model to the native patient tissue.

8. The method of claim 6, wherein the step of transferring the clinically useful information embodied in the information feature includes the step of generating at least one patient-specific surgical aid via interaction with the physical native tissue model and with the information feature.

9. The method of claim 1, including the steps of:
providing a prosthetic implant to be installed in the native patient tissue; and
including in the physical native tissue model, as generated, an information feature structure replicating at least a portion of the implant in a preoperatively planned installed position.

10. The method of claim 1, wherein the step of generating a physical native tissue model of a native patient tissue includes the step of generating a physical native tissue model of a partial native patient tissue, the method including the steps of:
providing a holder base representing a portion of a native patient tissue;
mating the physical native tissue model of the partial native patient tissue with the holder base;
referencing the mated physical native tissue model of the partial native patient tissue and holder base; and
exchanging the physical native tissue model of the partial native patient tissue upon the holder base for another physical native tissue model of the partial native patient tissue.

11. An apparatus for assisting a user with surgical implementation of a preoperative plan, the apparatus comprising:
a physical native tissue model of a native patient tissue, the physical native tissue model including at least one primary patient tissue area including a surface of interest, and at least one secondary patient tissue area including no surfaces of interest; and
at least one information feature providing clinically useful information to the user, the information feature being included in the physical native tissue model as generated;
wherein the surface of interest is a surface upon/into which a prosthetic device is to be placed or a surface which is to be the main subject of substantially permanent physical modification during a surgical procedure in an effort to provide therapeutic benefit to the patient;
wherein the information feature is any physical feature or characteristic of the physical native tissue model which signifies or communicates the clinically useful information to the user; and
wherein the information feature is substantially separated from the surface of interest.

12. The apparatus of claim 11, wherein the physical native tissue model includes a base surface for engaging a supporting structure and the information feature is a predetermined orientation of the base surface which is operative to position at least one surface of interest in a predetermined orientation in space when the base surface is engaged with the supporting structure.

13. The apparatus of claim 12, wherein the predetermined orientation of the base surface is chosen to dictate a clinically useful placement of a landmark into engagement with the physical native tissue model when the landmark is located orthogonally to the supporting structure.

14. The apparatus of claim 11, wherein the physical native tissue model of the native patient tissue is a tangible representation of a virtual model of the native patient tissue.

15. The apparatus of claim 11, wherein the information feature indicates a desired placement for a landmark, the landmark indicating at least one of a marking location and a marking trajectory to which reference is made during surgical modification of the native patient tissue.

16. The apparatus of claim 15, wherein the clinically useful information embodied in the landmark is transferred from the physical native tissue model to the native patient tissue during a surgical procedure.

17. The apparatus of claim 16, wherein a reusable surgical instrument is adjusted based upon the relationship of the landmark to the physical native tissue model to transfer at least a portion of the clinically useful information embodied in the landmark from the physical native tissue model to the native patient tissue.

18. The apparatus of claim 16, wherein at least one patient-specific surgical aid, containing at least a portion of the clinically useful information embodied in the landmark, is generated via interaction with the physical native tissue model and with the landmark.

19. The apparatus of claim 11, including a prosthetic implant to be installed in the native patient tissue, and wherein an information feature structure replicating at least a portion of the implant in a preoperatively planned installed position is included in the physical native tissue model, as generated.

20. The apparatus of claim 11, including a holder base and wherein the physical native tissue model of the native patient tissue is a physical native tissue model of a partial native patient tissue, the holder base selectively accepting the physical native tissue model of the partial native patient tissue in a mating relationship, the physical native tissue model of the partial native patient tissue being selectively replaced with another physical native tissue model of a partial native patient tissue upon the holder base.

21. A method of preoperative planning for assisting a user with surgical implementation of a preoperative plan, the method comprising the steps of:
generating a physical native tissue model of a native patient tissue, the physical native tissue model including at least one surface of interest and a base surface, spaced apart from the surface of interest, for engaging a supporting structure; and
including in the physical native tissue model, as generated, at least one information feature providing clinically useful information to the user;
wherein the information feature includes at least one of:
a landmark indicating at least one of a marking location and a marking trajectory to which reference is made during surgical modification of the native patient tissue, the landmark being spaced apart from the surgical modification location,
a predetermined orientation of the base surface which is operative to position at least one surface of interest in a predetermined orientation in space when the base surface is engaged with the supporting structure, and
a replica of at least a portion of a prosthetic implant in a preoperatively planned installed position.

22. The method of claim 21, including the step of transferring the clinically useful information embodied in the information feature from the physical native tissue model to the native patient tissue during a surgical procedure.

23. The method of claim 22, wherein the step of transferring the clinically useful information embodied in the information feature includes the step of adjusting a reusable surgical instrument to transfer at least a portion of the clinically useful information embodied in the information feature from the physical native tissue model to the native patient tissue.

24. The method of claim 22, wherein the step of transferring the clinically useful information embodied in the information feature includes the step of generating at least one patient-specific surgical aid via interaction with the physical native tissue model and with the information feature.

25. The method of claim 21, wherein the step of providing a physical native tissue model of a native patient tissue includes the steps of:
creating a virtual model of a native patient tissue; and
creating a physical native tissue model of the native patient tissue as a tangible representation of the virtual model of the native patient tissue.

26. A method of preoperative planning for assisting a user with surgical implementation of a preoperative plan, the method comprising the steps of:
generating a physical native tissue model of a native patient tissue, the physical native tissue model including at least one surface of interest and a base surface, spaced apart from the surface of interest, for engaging a supporting structure; and
including in the physical native tissue model, as generated, at least one information feature providing clinically useful information to the user;
wherein the clinically useful information is information other than a desired location for material modification of the native patient tissue.

27. The method of claim 26, including the step of transferring the clinically useful information embodied in the information feature from the physical native tissue model to the native patient tissue during a surgical procedure.

28. The method of claim 27, wherein the step of transferring the clinically useful information embodied in the information feature includes the step of adjusting a reusable surgical instrument to transfer at least a portion of the clinically useful information embodied in the information feature from the physical native tissue model to the native patient tissue.

29. The method of claim 27, wherein the step of transferring the clinically useful information embodied in the information feature includes the step of generating at least one patient-specific surgical aid via interaction with the physical native tissue model and with the information feature.

30. The method of claim 26, wherein the step of providing a physical native tissue model of a native patient tissue includes the steps of:
creating a virtual model of a native patient tissue; and
creating a physical native tissue model of the native patient tissue as a tangible representation of the virtual model of the native patient tissue.

31. The method of claim 1, wherein the primary patient tissue area represented upon the physical native tissue model is a positive reproduction of the native patient tissue.

32. The apparatus of claim 11, wherein the primary patient tissue area represented upon the physical native tissue model is a positive reproduction of the native patient tissue.

33. The method of claim 21, wherein the primary patient tissue area represented upon the physical native tissue model is a positive reproduction of the native patient tissue.

34. The method of claim 26, wherein the primary patient tissue area represented upon the physical native tissue model is a positive reproduction of the native patient tissue.

* * * * *